(12) United States Patent
Tsoukalis

(10) Patent No.: US 10,874,795 B2
(45) Date of Patent: Dec. 29, 2020

(54) UPGRADE SMART KIT FOR CONVENTIONAL LARGE VOLUMETRIC PUMPS

(71) Applicant: Micrel Medical Devices S.A., Gerakas (GR)

(72) Inventor: Achilleas Tsoukalis, Anayvyssos Attiki (GR)

(73) Assignee: Micrel Medical Devices S.A., Gerakas (GR)

( * ) Notice: Subject to any disclaimer, the term of this patent is extended or adjusted under 35 U.S.C. 154(b) by 0 days.

(21) Appl. No.: 16/023,860

(22) Filed: Jun. 29, 2018

(65) Prior Publication Data
US 2019/0001057 A1  Jan. 3, 2019

(30) Foreign Application Priority Data

Jun. 29, 2017 (EP) ..................................... 17178611
Aug. 4, 2017 (EP) ..................................... 17185028

(51) Int. Cl.
*G06K 7/08* (2006.01)
*A61M 5/172* (2006.01)
(Continued)

(52) U.S. Cl.
CPC ............ *A61M 5/172* (2013.01); *A61M 5/142* (2013.01); *A61M 5/148* (2013.01);
(Continued)

(58) Field of Classification Search
CPC ...... A61M 5/172; A61M 5/142; A61M 5/148; A61M 5/1684; A61M 5/1689; A61M 5/16895; G06K 7/10366
(Continued)

(56) References Cited

U.S. PATENT DOCUMENTS 5,135,485 A   8/1992   Cohen et al.
2003/0135388 A1*   7/2003   Martucci ............... A61M 5/142
                                                                    705/2
(Continued)

FOREIGN PATENT DOCUMENTS

EP   2 987 517   2/2016
WO   WO 2006/122167   11/2006
WO   WO 2017/055441   4/2017

OTHER PUBLICATIONS

Extended European search report in corresponding European Application No. 18180930.2, dated Nov. 27, 2018 (9 pages).

*Primary Examiner* — Karl D Frech
(74) *Attorney, Agent, or Firm* — Bookoff McAndrews, PLLC

(57) ABSTRACT

An infusion safety device comprises a tag reader which is adapted to read a medication tag provided at an infusion medication reservoir, in particular during the whole infusion and a processing unit which is connected with said tag reader and is provided to be connected with an infusion pump in which an infusion protocol is stored and is adapted to recognize a change of the medication reservoir, to read out the infusion protocol from the infusion pump, to cause said tag reader to carry out a reading operation at the latest in case it recognizes a change of the medication reservoir and to give an alarm in case there is no match between the medication read by said tag reader and the medication required by the infusion protocol.

39 Claims, 8 Drawing Sheets

(51) Int. Cl.
*A61M 5/168* (2006.01)
*G06K 7/10* (2006.01)
*A61M 5/148* (2006.01)
*A61M 5/142* (2006.01)

(52) U.S. Cl.
CPC ........ *A61M 5/1684* (2013.01); *A61M 5/1689* (2013.01); *A61M 5/16895* (2013.01); *G06K 7/10366* (2013.01); *A61M 5/16845* (2013.01); *A61M 5/16881* (2013.01); *A61M 2205/12* (2013.01); *A61M 2205/125* (2013.01); *A61M 2205/14* (2013.01); *A61M 2205/18* (2013.01); *A61M 2205/3306* (2013.01); *A61M 2205/3327* (2013.01); *A61M 2205/3375* (2013.01); *A61M 2205/3386* (2013.01); *A61M 2205/3393* (2013.01); *A61M 2205/3569* (2013.01); *A61M 2205/584* (2013.01); *A61M 2205/587* (2013.01); *A61M 2205/6018* (2013.01); *A61M 2205/6054* (2013.01); *A61M 2205/6072* (2013.01); *A61M 2205/702* (2013.01); *A61M 2205/75* (2013.01); *A61M 2205/8206* (2013.01); *A61M 2205/8212* (2013.01)

(58) Field of Classification Search
USPC ...................................................... 235/451
See application file for complete search history.

(56) References Cited

U.S. PATENT DOCUMENTS

| 2005/0172712 | A1 | 8/2005 | Nyce | |
| 2010/0001838 | A1* | 1/2010 | Miodownik | G06Q 10/06 340/10.1 |
| 2011/0205074 | A1 | 8/2011 | Feng et al. | |
| 2015/0001285 | A1* | 1/2015 | Halbert | G16H 10/65 235/375 |
| 2016/0123320 | A1 | 5/2016 | Tsoukalis | |

* cited by examiner

UPGRADE SMART KIT FOR CONVENTIONAL LARGE VOLUMETRIC PUMPS

BACKGROUND

Conventional Large Volumetric Pump (LVP) devices of the prior art comprise an electromechanical pump mounted on a pole clamp and plugged to the mains, and also having as an accessory an electro-optic drip counting unit connected with a cable in case the pump needs to run in drops/minute rather than ml/h, while from the top of the same pole a drug or medication container or reservoir is hanged down and spiked by a pump's infusion set, having usually a spike/drip chamber combination for this doing, on which said drip counter unit is gripped sending drop per drop information to the pump.

Smart pumps additionally have a barcode reader with a cable to read drug or medication tags or labels and to correlate the drug to downloaded drug libraries for medication error prevention by using protocol limits per care area and drug. But it is reported in literature that with scanning a medication an error can occur by connecting a line coming from another pump instead of from the intended one, just because there is no safe link between the medication, the barcode reader, the pump and its infusion line. So, smart pumps have the risk today to cause medication errors, and there are high numbers of reported deaths from this. Especially piggyback infusions are infusions from one of two upstream connected infusion lines with one of them at a higher level infusing due to hydrostatic pressure difference. The nurses, however, forget to change the protocols stored in the pump after elevating the one reservoir and lowering the other one.

Air from an empty medication container may enter the line, so that the patient is protected by an Air In Line detector at the pump which is arranged about one meter below the container; in such an alarm case, the nurse needs to disconnect the line from the patient and purge it again after replacement of the container. The drop counting unit can give an alarm if it detects no drops during infusion, but sometimes low level of liquid in a drip chamber can allow air to enter the line without interruption of the feeding of drops. The emptying of the reservoir in the prior art is calculated from a subtraction of the Volume Infused (VI) from the Volume To Be Infused (VTBI). Today hydration fluids are delivered by gravity in most cases, just because the setting of a gravity set is easier.

Barcode labeling is by far the most common pharmaceutical drug and solution encoding system that has lowest cost (just printing) and due to its QR form has a small size. A change of a pharmaceutical file from an existing one to a new one by repositioning or providing an extra barcode at a specific location results in lowest costs for pharmaceutical companies to comply with safety rules according to the present patent application and saves lives of thousands of patients.

SUMMARY OF THE INVENTION

In order to overcome the aforementioned drawbacks of the prior art and to achieve further objects, in accordance with a first aspect of the present invention, there is provided an infusion safety device comprising a tag reader which is adapted to read a medication tag provided at an infusion medication reservoir, in particular continuously during the whole infusion, characterized by a processing unit which is connected with said tag reader and is provided to be connected with an infusion pump in which an infusion protocol is stored and is adapted to recognize a change of the medication reservoir, to read out the infusion protocol from the infusion pump, to cause said tag reader to carry out a reading operation at the latest in case it recognizes a change of the medication reservoir and to give an alarm in case there is no match between the medication read by said tag reader and the medication required by the infusion protocol. The infusion safety device comprises one or more of the following three units: A flow sensor, an active valve or the pump having an infusion tubing segment (or a pump controller with a disposable pump mechanism) itself at the proximity of the reservoir tag which therefore can be read automatically without human action anytime.

Further preferred embodiments and modifications are defined by the dependent claims.

In accordance with a second aspect of the present invention, there is provided an infusion safety device comprising a medication tag reader having an optical unit which is adapted to read a tag provided as a barcode on the surface of an infusion medication reservoir, or its border, characterized by an adjustment equipment which is adapted to adjust at least a part of said optical unit so as to enable it to read the barcode.

In a first preferred embodiment, said optical unit comprises a camera which is adapted to directly face the barcode, and said adjustment equipment is adapted to adjust the viewing angle and/or the position, in particular the height, of said camera relative to the barcode. Accordingly, in order to directly face the barcode, the camera can be arranged in a vertical orientation to face or to have a view in an essentially vertical direction upwards to a barcode positioned at the medication reservoir accordingly, i.e. arranged in an essentially horizontal orientation or plane, or alternatively the camera can be arranged in an essentially horizontal orientation so as to face or have a view in an essentially horizontal direction to a barcode arranged at the medication reservoir in an essentially vertical orientation or plane, e.g. at a side of the medication reservoir.

In an alternative second preferred embodiment, said optical unit comprises at least one mirror, and said adjustment equipment is adapted to adjust the viewing angle and/or the position, in particular the height, of said mirror relative to the barcode, wherein according to a preferred modification of this embodiment said optical unit comprises a periscope including said mirror, wherein said adjustment equipment is adapted to adjust the viewing angle and/or the position, in particular the height, of said periscope relative to the barcode, and further comprises a camera pointing to said mirror. Accordingly, the camera can preferably be arranged in a vertical orientation so as to point to the mirror which is located above the camera and results in a reflection of the view of the camera to the barcode which is arranged at the medication reservoir in an essentially vertical orientation or plane, e.g. at a side of the medication reservoir. According to a further preferred modification, the mirror or, if the mirror is part of a periscope, the periscope is removably provided, so that in case of a removal of the mirror or the periscope the camera can also be used to read a horizontally oriented medication tag facing then downwards to the camera.

Further preferred embodiments and modifications of the second aspect of the present invention are defined in the dependent claims.

There can also be a combination of the first aspect and the second aspect of the present invention, wherein further preferred embodiments and modifications applying to each of both the first and second aspects of the present invention are defined in the dependent claims.

According to a third aspect of the present invention, there is provided an infusion safety device comprising a medication reservoir which includes a main volume portion, characterized by a lower volume portion fluidly communicating with said main volume portion and arranged below said main volume portion with the medical reservoir being in its operational position, wherein said lower volume portion has a width depending upon the total volume of the medical reservoir so that it is larger with a bigger total volume and smaller with a smaller total volume, wherein said lower volume portion has a predetermined height which is the same with all medication reservoirs irrespective of their total volume, and wherein said lower volume portion is provided as a low level volume compartment defining a predetermined low volume level for indication of a near end of an infusion as an alarm criterion.

Accordingly, when using different medication reservoirs having a different total volume the predetermined height of the lower volume portion is the same and, hence, defines a standard height for the definition of the predetermined low volume level, whereas the width of the lower volume portion depends upon the total volume of the medical reservoir so that it is larger with a bigger total volume and smaller with a smaller total volume and the required difference of a near end of infusion volume per total volume of the respective reservoir is achieved by a difference in the width of the lower volume portion. So, the relation between the near end of infusion volume and the total volume of the respective medication reservoir can optionally be more or less equal or similar for larger volume reservoirs or smaller volume reservoirs. Since the predetermined lower volume level in the lower volume portion is provided for indication of a near end of an infusion used as an alarm criterion, the near end of an infusion volume is an alarm volume.

Further preferred embodiments and modifications of the third aspect are defined in the dependent claims.

Moreover, there can also be a combination of the third aspect with the first aspect and/or the second aspect of the present invention.

Finally, according to a fourth aspect of the present invention, there is provided an infusion system comprising the device according to the first and/or the second aspect of the present invention as well as an infusion medication reservoir, in particular according to the third aspect of the present invention, which is provided with a medication tag.

Further preferred embodiments and modifications are defined in the dependent claims.

The present invention provides safety means to automate the infusion setup and to eliminate any user error in the infusion management using smart pumps or devices by providing drug label reading in correlation with drug labeling placed in a way to be read by devices anytime at start or during infusion.

Due to the fact that the medication error prevention at 100% is a social urgent need and conventional LVPs are installed in large quantities, the present invention intends to provide a novel device accessory and infusion set that can improve and upgrade existing or new conventional type LVPs, concerning medication error prevention, with a direct reading of a drug label, easiness of setup and use, accuracy and infusion linearity.

The present invention deals with solve both safety and usability of the aforementioned procedure and provides easy to implement solutions for 100% medication error prevention and even avoids air to enter the upstream line for conventional LVPs.

Further, the present invention provides an easy way to deliver fluids by gravity with just a rate programming.

According to the present invention means are provided to give a warning whenever the volume of the drug in the reservoir becomes low so that the nurse has enough time to change the reservoir even if she does not program the VTBI (Volume To Be Infused). Safety is assured when a label reading device is in direct reading distance and position with a machine-readable drug label during the whole infusion combined with one of three safety devices being an infusion pump or module, a flow sensor or an active valve.

The present invention provides an accessory device or kit for both conventional LVPs and pumps hanging on reservoir for piggyback infusions A cable for a serial communication with the pump and the accessory hanging on a drip chamber, wherein the communication can also be wireless, has a number of sensors to make safe both conventional pumps and piggyback infusions. For doing so, provided is a drip sensor (flow detector), a low level detector detecting when air is about to enter the line, an active valve that can comprise pinching fingers to be closed by a micro-motor at a lower end of the upstream tubing line, a camera for QR barcode reading, a vibration sensor like an accelerometer or tilt sensor, a perpendicularity/inclination sensor or a combination of the above to sense and to algorithmically determine when a connector or spike is removed and replaced so as to know when a reservoir is changed. It may also have a (preferably capacitive or ultrasound) level detector for an extra lower part of the reservoir defining a so-called Near End Of Infusion Volume that helps pump alarm for a change of the bag, container or reservoir early enough.

The accessory for a conventional pump can check the compatibility of a drug tag with a protocol any time before or during the infusion, can check if the (electric) connection of the accessory that is reading the tag or label is the same as the fluid connection (delivering drug) by sensing the start of the dripping when the pump starts, or stop momentarily the infusion until the dripping stops, or for piggyback infusions that start anytime when the reservoir is elevated. Namely, in piggyback infusions two reservoirs connected by a Y connection to a single pump are arranged one higher than the other, wherein only the higher one having higher hydrostatic pressure infuses, and fatal errors occur when a change in the height of a reservoir does not result in a corresponding change the protocol in the pump. According to the present invention, one conventional pump has two drug safety kit devices as described above attached to two drip chambers with a direct reading of respective drug tags, and an alternation of the protocol is automatic when drug dripping sensors indicate an alternation of the infusion from one drug to the other. The accessory kit also having a low level detector assures conventional pumps not to allow air to enter the line resulting in stopping the infusion with an alarm.

The safety accessory kit can use (if configured on the pump) the active valve for an automatic alternation of the infusions between the primary reservoir and the secondary reservoir, while both drugs are at the same level, by activating (opening) the valve for the reservoir containing the drug to be infused. The pump has also a user interface (UI) that can program an alternation of the infusion or multiple infusions as with a cancer chemotherapy wherein eight drugs are sequentially administered. This assures a safety of drug to protocol (barcode reading) and protocol to infusing reservoir check by the pump. In case the valve is not used, when a nurse elevates the secondary reservoir, dripping will show it, and the pump automatically switches the protocols from the primary to the secondary reservoir by simultaneously giving a warning. Even more, by knowing the infusion rate, the drop counting in both the drip chambers converted to rate in ml/h should match the infusion rate; if not, possibly the elevation is not enough and both reservoirs are infusing, resulting in generating an alarm according to another aspect of the present invention. According to the present invention means are provided to early detect excessive air in a drip chamber and to give an alarm in such case so as to prevent air to enter the infusion line. Additionally the present invention provides a medication reservoir that preferably has a lower restricted width part that at some level contains liquid with a remaining volume being equal to the near end infusion alarm volume so that, if sensed, the nurse is alarmed before it is too late for a change. The kit has for this sensing a reservoir level detector at the near end level mark. The kit informs the pump about reservoir levels with first a near end level sensed from the top of the lower near end volume, then a stop of dripping results in a second alarm indicating the end of volume in the reservoir which alarm is given by the pump wherein the pump may continue infusing or not depending upon the policy preferred, and a third alarm indicating a low level in the drip chamber that definitively will stop infusion in the light of that the end of volume is reached and there is now a risk of air entering the line. So, the present invention provides the generation of an "empty reservoir" alarm from the pump before air enters the line and the generation of a "near end of infusion" alarm from a reservoir reading process.

The barcode at the reservoir used for the present invention does not necessarily exactly correspond to the one written on the drug's label and does not need to follow the standard labeling rules. Its contents can alternatively or additionally be stored in RFID/NFC passive or active labels. Since it is for three cases of content description—pre-filled reservoirs, added drugs on pre-filled originally labeled containers, and completely compounded drugs—it is preferably a QR (two dimensional) barcode.

For pre-filled drugs or fluids due to the National Drug Code (NDC) the pump can retrieve drug attributes from a server or a downloaded drug library.

For additional medication in pre-filled fluid containers (dextrose or saline) the NDC of the original fluid and the NDC of all additional drugs and respective concentrations includes an expiry date for the drug and a production number of the reservoir if any. Standards issued from the Institute for Safe Medication Practises (ISMP) regulate this process, and software is available on the market for compounding labeling.

The same applies to empty reservoirs which are filled with drugs and solutions by a compounder like a pharmacist in an industrial scale or a location where specific preparation information can be retrieved (web or other).

QR barcodes and also RFID/NFC tags or labels have enough content space to contain the above, which give additional information of what can be taken from drug libraries (drug libraries do not comprise any expiry dates).

The location of the barcode and/or RFID/NFC tag is nonstandard and can be preferably on a vertical plate over a connecting tube facing down. With such an embodiment the label can be folded in parallel to the reservoir and unfolded (automatically by spring action or by hand) to a vertical orientation when it is to be used, and a click may then hold the label in this position to avoid false alarms if out of view from a reader. A stop at the connecting tube cap may keep the label parallel to the reservoir down to an opening cap for the insertion of a spike when it unfolds to a vertical orientation, preferably by spring action automatically. For compounding, a label holding fastener at a connecting reservoir tube that cannot be opened after placement is used. One option is a saw tooth strip fastener as for electrical cables. It can also be at the same location as the plate parallel to the reservoir border pattern wherein the label can be read through a periscope from below or by a camera facing it with a wide angle short range or close-up lens, i.e. on an extension below the border, on the top border near a reservoir hanging hole, or anywhere on the reservoir surface including its borders and the periphery of the reservoir. The barcode label can be used for any size of the reservoir and positioned at the same height and width (left or right) on the walls, the border or the top area of the reservoir, regardless of the size of the reservoir. The pump itself or the accessory kit is fluidly connected through a connecting point which is usually provided as a protruding tube with a spike or connector at a known position in reference to the reservoir dimensions so that the label can be read at the same location regardless of the size of the reservoir. The barcode label can be transparent on its "white" areas, so that ambient light pass through and black parts are read by the camera without the need of front illumination that would consume energy. This is easily done by printing black areas of the barcode directly on a clear plastic portion or border of the reservoir itself or by using clear plastic for a printed adhesive label. Inventively, the pump controller can additionally evaluate the image without illumination if it is readable, and if not, it illuminates the label, a procedure that reduces power needed for each reading. The illumination wavelength is preferably in an extreme region of the visible light in order to reduce patient annoyance, since a position tracking with visible light is not needed for automatic reading of the present invention.

The tag can also be a memory chip of standard or organic electronics that can be placed at or near the fluid connector and powered and read serially by contacts at the fluid connector from the pump side anytime so that a disconnection or connection is immediately sensed. The pump gives an alarm if after programming at review of 5R (Right patient, Right drug, Right protocol, Right time, Right delivery route) or at start it does not read the tag, so that it needs to assign a person to get responsibility of infusing without tag reading, wherein in such a case a double nurse verification may be needed.

An application on a personal computer or a mobile device can read a tag at a reservoir in a pharmacy and print it as QR code by a pharmacy printer so as to be self-adhesively placed on the reservoir itself at a specific location in reference with the connecting tube so to be machine-readable anytime or at tag plates in a perpendicular or horizontal orientation, or can fold in half, adhesively glued on front and back side of a lower border extending downwards to the position of the pump or an accessory device camera. So conventional initially pre-filled reservoirs can be used safely with the present invention.

Preferably, it is provided a touch display, in particular an extremely low power and weight e-paper color or black and white, allowing gestures that ease programming in cooperation with the described devices that automate many tasks so that finally the pump is extremely easy to use with a very low risk of erroneous handling (excellent usability).

In the following, preferred embodiments of the present invention will be described with reference to the accompanying drawings.

DESCRIPTION OF PREFERRED EMBODIMENTS

Figure 1:
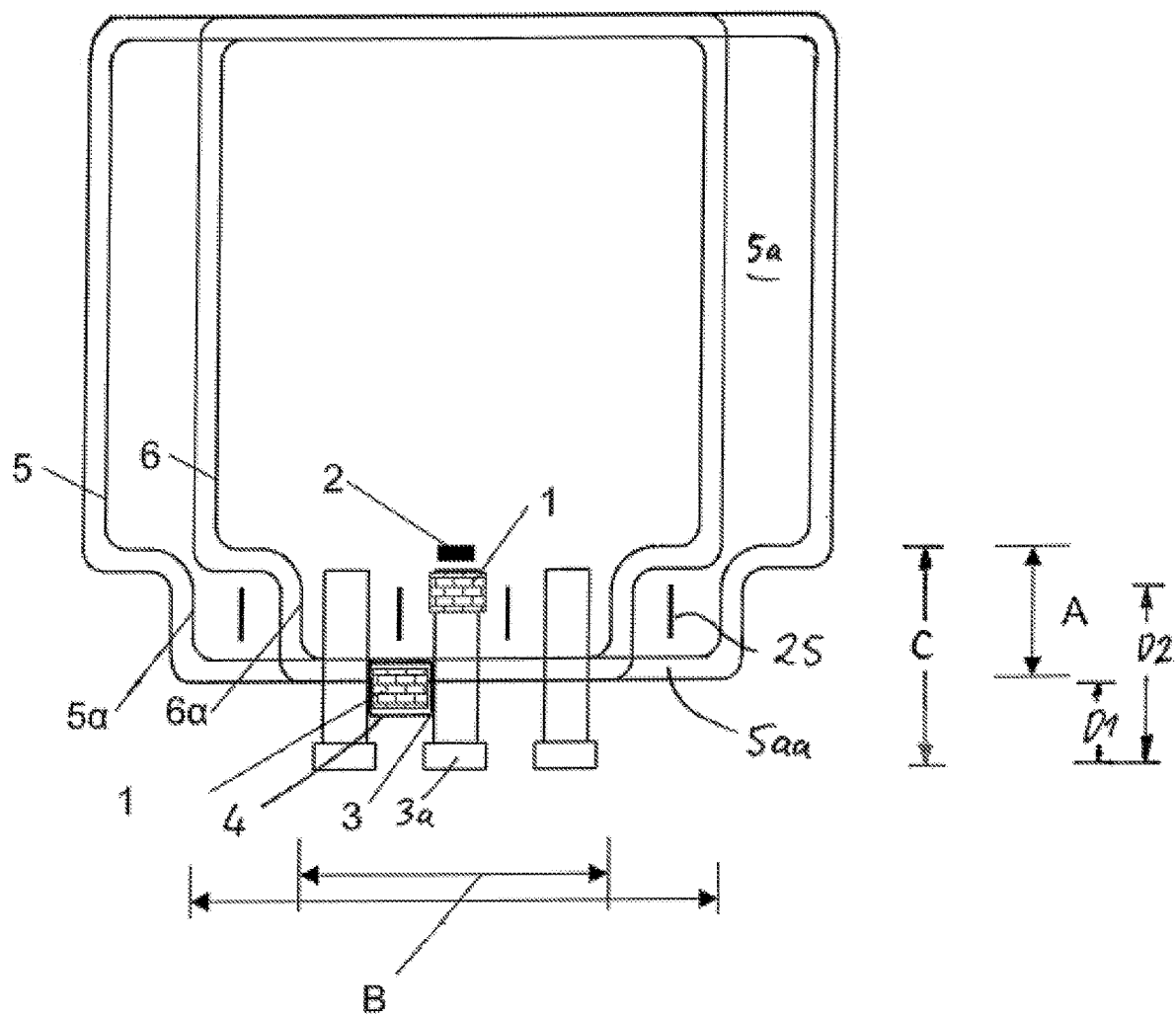
FIG. 1 schematically shows a medication reservoir illustrated in two different embodiments one in the other.

FIG. 1 shows as an example two different embodiments of a medication reservoir 5 and 6 illustrated one in the other and having a different size, wherein the reservoir 5 is relatively large and comprises a lower end portion 5a defining a so-called near end volume and the reservoir 6 is smaller and comprises a lower end portion 6a defining a near end volume which has a smaller width B than, but the same height A as the near end volume of the lower portion 5a of the reservoir 5, while above said lower portion 5a, 6a the reservoir 5, 6 includes a main portion 5b, 6b. For both these reservoirs 5, 6 a sensing is provided at the same position C relative to the lower part 3a of a connection element 3 which position defines a constant reservoir low level or Near End of Infusion sensor reading point 2. The placement of a barcode 1, preferably a QR label, is provided at the same position D1 or D2 relative to the lower part 3a of the connection element 3, e.g. at the lower edge or border of the reservoir 5, 6 wherein preferably the barcode is placed on a tongue 4 or at the lower edge or border of the reservoir 5, 6 and hangs down therefrom (position D1), or at the connector 3, in particular at its top (position D2), wherein both these exemplary alternative embodiments are shown in FIG. 1. Moreover, in the shown embodiment the lower portion 5a, 6a of the reservoir 5, 6 are provided with vertical bond strips 25 on its walls so as to define an array of vertical tubes open at their bottom for a communication with the fluid from below and on top for an escape of trapped air to the main portion 5b of the reservoir 5 and for filtering liquid movement from one side to the other.

Figure 2:
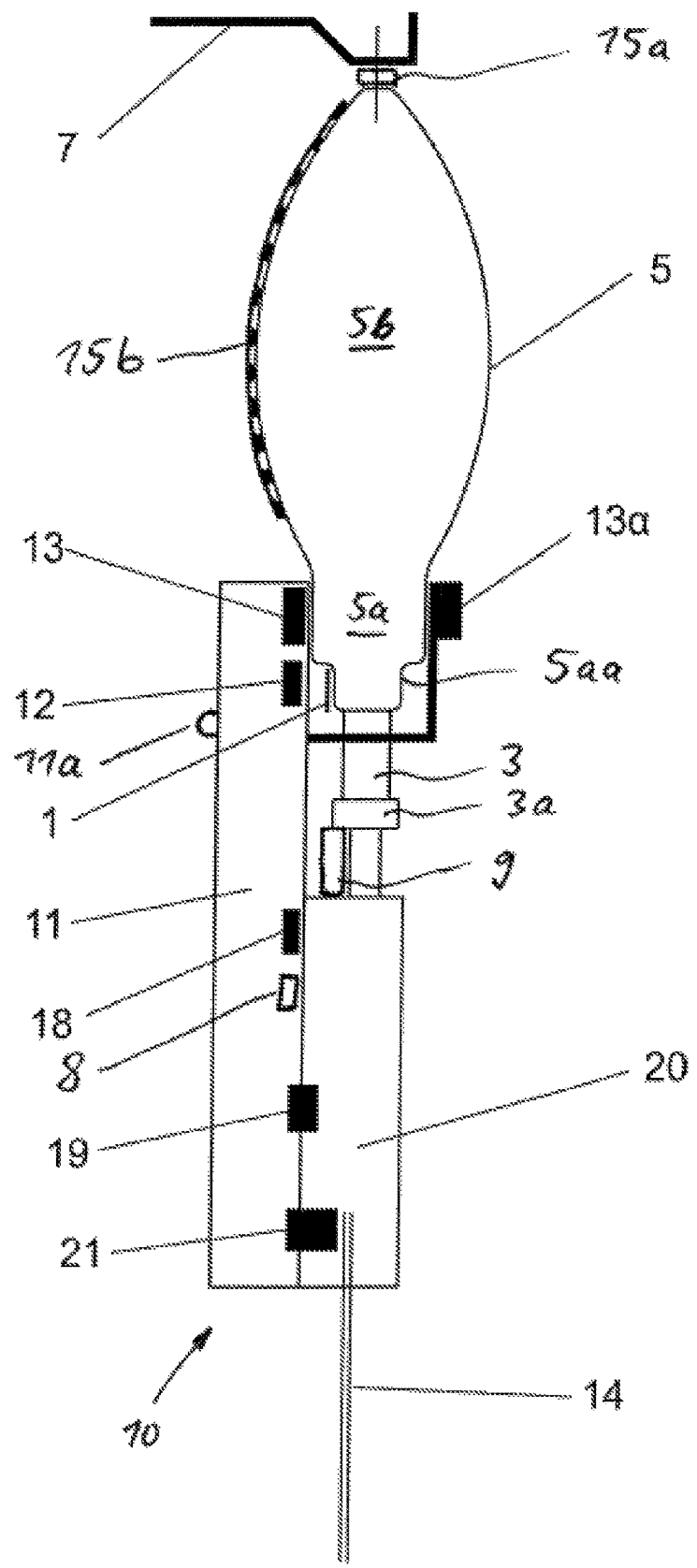
FIG. 2 schematically shows a safe infusion pump/reservoir combination according to a first preferred embodiment.

FIG. 2 shows a safe infusion pump/reservoir combination, wherein a reservoir 5 hangs down from a pole 7. An infusion pump controller 11 is attached to a drip-chamber-peristaltic-pump part 10 which is embodied as a cartridge and includes a square type drip chamber 20 and a peristaltic pump mechanism (not shown). The pump controller 11 comprises a tilt and/or accelerometer sensor 8. A contact sensor 9 is provided to detect a contact with an infusion system and/or with the connector 3 in order to determine an unplugged or plugged state. At the pump controller 11 it is provided an illuminating indicator 11a, preferably a light emitting diode, which is adapted to flash light in a first, preferably green, color for each drop detected in the infusion state and in a second, preferably red, color in an alarm state. A reservoir low level sensor 13 is provided at the top of the controller 11 and adjacent to the lower portion 5a of the reservoir 5 so as to sense the existence of fluid at the reading point 2 (FIG. 1). The sensor 13 can be preferably embodied as a capacitive sensor with an element 13a as holder arranged on the other (or flip) side of the reservoir 5 or as an ultrasound sensor with an element 13a as a second detector (receiver or transmitter) arranged on the other side of the reservoir. Further, a barcode camera 12 with a close-up lens is also provided at the top of the controller 11 and faces a barcode 1 which is fastened at the lower edge or border 5aa of the lower portion 5a of the reservoir 5, to read the barcode 1. A load cell 15a measuring weight electrically/electronically connected with the whole assembly hangs down from the pole 7 and the reservoir 5 from said load cell 15a, so that it can monitor any weight changes of the hanged reservoir 5. A long capacitive fluid level detector 15b extending from the top to the bottom of the reservoir 5 is attached at a side of the reservoir 5 and provided with a plurality of capacitive conductive pattern pairwise elements (US2005/0172712A1) connected in parallel so as to enhance their capacitance and separated from each other in height in an equidistant arrangement, wherein the detector 15b is preferably easily bendable so as to follow a curvature of the reservoir and maintain contact with its surface all time, and an elastic belt may be provided wherein the conductive patterns and connecting conductors (tinsel wire for bending without breaking) are embedded in the woven material of said belt so that when it senses full liquid due to an it increased capacitance in contrast to a case when the reservoir 5 includes less liquid or is empty, and therefore can transmit to the pump controller an indication of what percentage of liquid is in the reservoir. A drip sensor 18 is provided at the controller 11 adjacent to the top of the drip chamber 20, to detect the presence of drops entering the drip chamber 20. A drip chamber low level sensor 19 is provided below the drip sensor 18 to detect a low level of fluid in the drip chamber 20. Moreover an air-in-line detector 21 is provided at a lower part of the spike-drip-chamber-peristaltic-pump cartridge 20 to detect air in a tube 14 at the downstream side of an infusion pump mechanism at the bottom of the cartridge not shown. The drip chamber is fluidly coupled upstream with the connector 3 of the reservoir 5 so that the whole spike-drip-chamber-peristaltic-pump part 20 and its attached pump controller 11 hangs down from the reservoir 5.

Figure 2A:
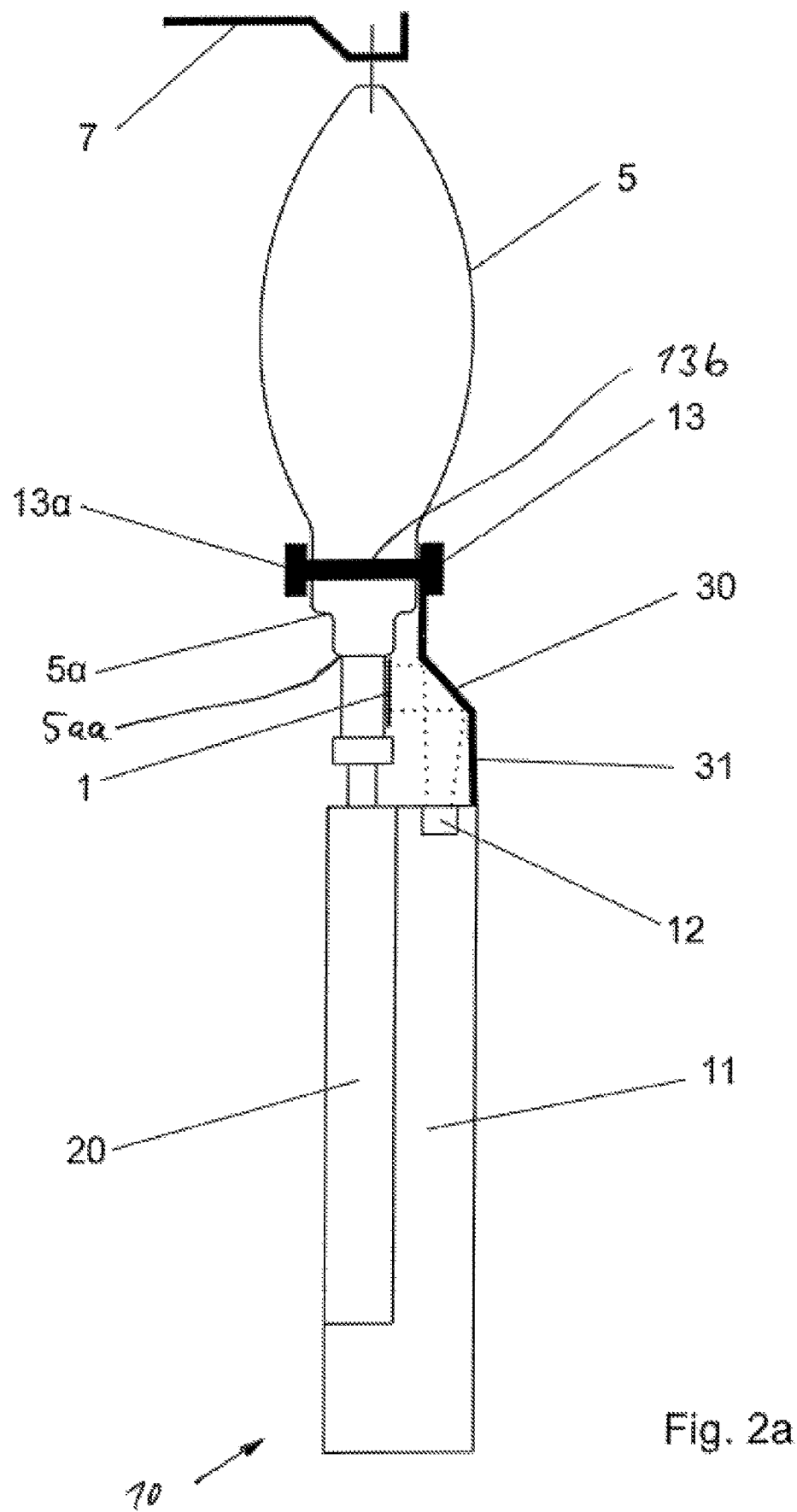
FIG. 2a schematically shows a safe infusion pump/reservoir combination according to a second preferred embodiment.

FIG. 2a shows a similar assembly which only differs from that of FIG. 2 in that the camera 12 is orientated so as to view upwards and a lever 31 is mounted at the top of the spike-drip-chamber-peristaltic-pump part 10 and comprises a 45 deg. inclined portion at which a mirror 30 is provided as a periscope to read the tag 1 which is placed at the tongue 4 fixed at the lower border 5aa of the lower portion 5a of the reservoir 5 and hanging down from it or is printed on the border 5aa itself. At the upper end of the lever 31 arranged is a low level detector which can be embodied as capacitive sensor alone or as an ultrasound sensor with a responder 13a on the opposite side of the reservoir wherein both elements 13 and 13a can be connected with each other by a connecting element 13b like an elastic belt as shown in FIG. 2a. As to all the other components shown in FIG. 2a, reference is made to the corresponding portions of the above description of FIG. 2. Finally, all further components shown in FIG. 2 but not shown in FIG. 2a can also be provided in the assembly of FIG. 2a, either only one of them or in a combination of some or all of them, wherein reference is made to the corresponding portions of the above description of FIG. 2.

Figure 3:
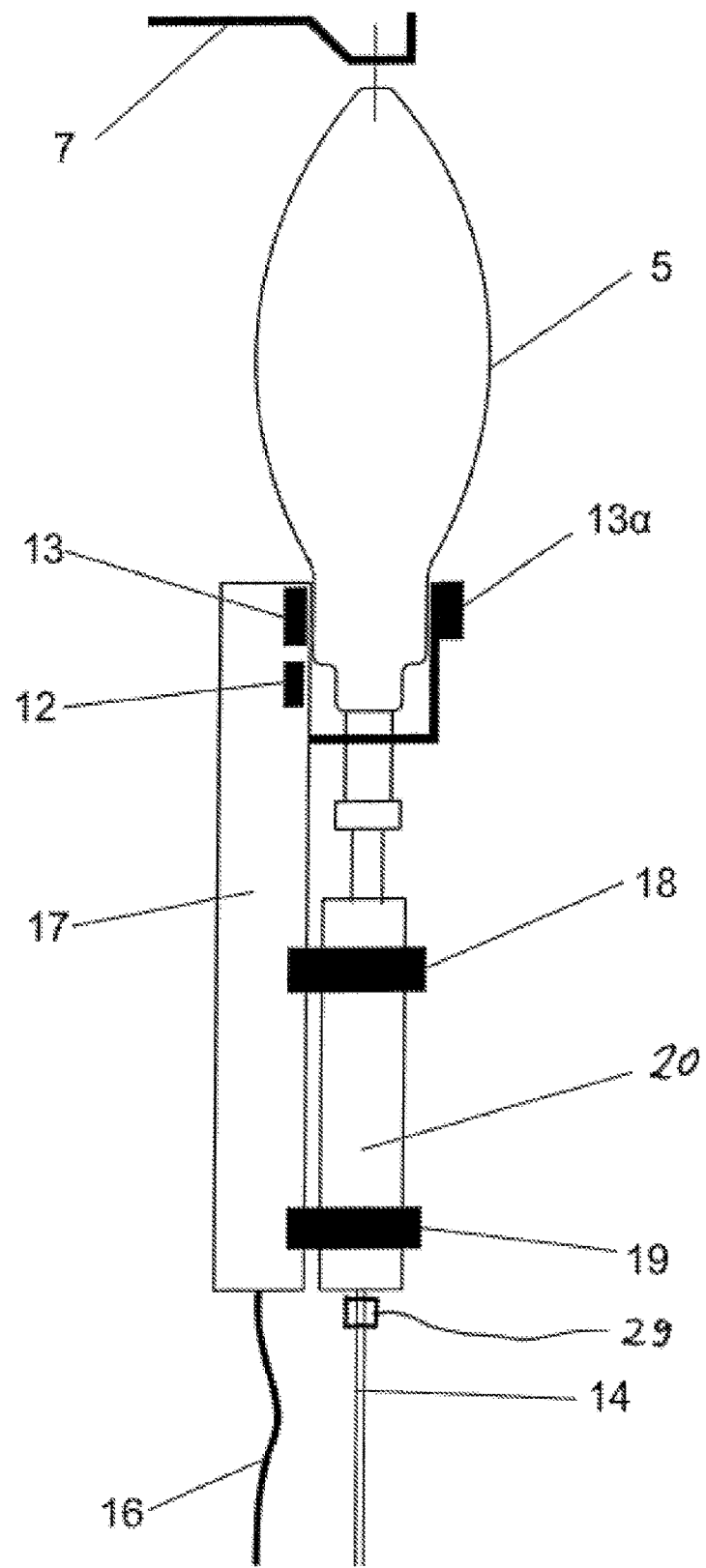
FIG. 3 schematically shows a safe infusion flow sensor/reservoir combination according to a third preferred embodiment comprising an infusion pump upgrade kit.

FIG. 3 shows a similar assembly as that of FIG. 2 but instead of a drip-chamber-peristaltic-pump part it is provided a separate drip chamber 20 and an infusion safety accessory kit 17 which is provided as an upgrade kit and fastened to a side of the drip chamber 20 which is embraced by the bodies of the sensors 18 and 19 as usual drip chamber drip counters. The infusion pump upgrade kit 17 comprises a barcode camera 12, a reservoir level sensor 13, a drip sensor 18 and a drip chamber low level sensor 19 wherein all said components are arranged in a similar manner as with the embodiment of FIG. 2 so that reference is made to the corresponding portions of the above description of FIG. 2. Further the infusion pump upgrade kit 17 comprises a communication cable 16 connected to a pump not shown. Moreover, in particular just downstream from the drip chamber 20, the infusion tube 14 is provided with an active valve 29. Finally, all further components shown in FIG. 2 but not shown in FIG. 3 can also be provided in the assembly of FIG. 3, either only one of them or in a combination of some or all of them, wherein reference is made to the corresponding portions of the above description of FIG. 2.

Figure 4:
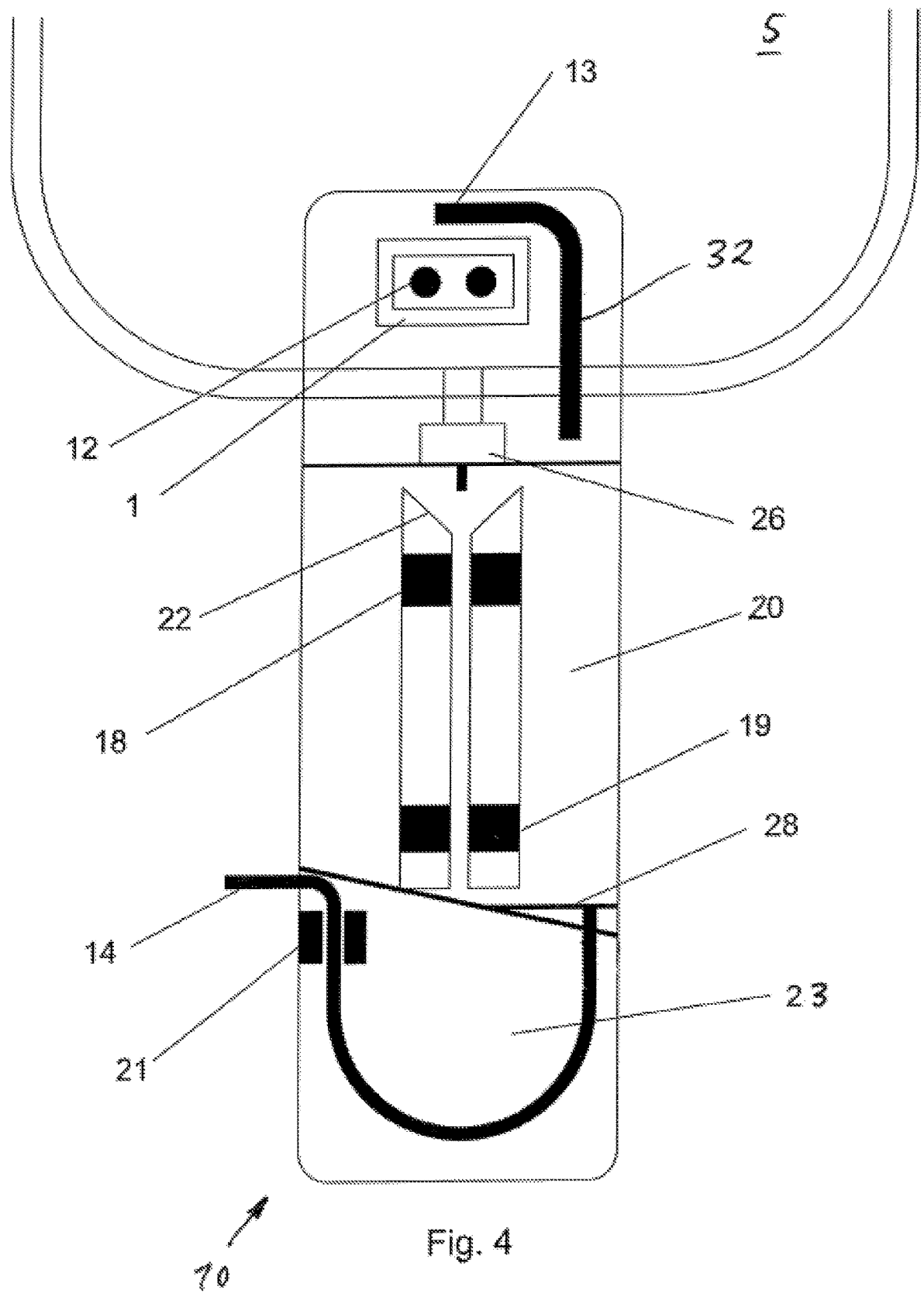
FIG. 4 schematically shows a back side of a drip-chamber-rotary-peristaltic-pump part provided as a consumable part according to a first preferred embodiment.

FIG. 4 shows a back side of the drip-chamber-rotary-peristaltic-pump part 10 which is embodied as a consumable cartridge and hangs down from the reservoir 5 therefore holding the attached drip-chamber-rotary-peristaltic-pump part 10 in position to read the barcode directly. On the top of the drip-chamber-rotary-peristaltic-pump part 10 a connector 26 for connection with the connector 3 (FIG. 1) of the reservoir 5, the camera 12 and the placement of a barcode 1 both shown from behind and a U-shaped arm 32 shown from the other side of the reservoir 5 and supporting the reservoir low level sensor 13 are provided. The middle portion of the drip-chamber-rotary-peristaltic-pump part 10 includes the drip chamber 20, a drop collector 22 just under a drop forming needle having an air passing path on top of it to allow formation of drops, upper drip detector cavities at which the drip sensor 18 (here embodied as a dual ultrasound head) is arranged and lower level detection cavities at which the drip chamber low level sensor 19 (here embodied as an ultrasound dual head 19) is arranged. The lower end of the drip-chamber-rotary-peristaltic-pump part 10 includes a rotary peristaltic mechanism 23 as described in EP 3 017 836 A1 and US 20160123320 A1 (shown simplified herein) with an Air In Line detector 21, a particles filter at a lower end 28 of the drip chamber 20 and an infusion tubing 14 connected to the drip chamber 20. Finally, in this embodiment the drip-chamber-rotary-peristaltic-pump part 10 forms a single piece cartridge snap-fitted behind the pump. As to all the other components shown in FIG. 4, reference is made to the corresponding portions of the above description of FIG. 2. Finally, all further components shown in FIG. 2 but not shown in FIG. 4 can also be provided in the assembly of FIG. 4, either only one of them or in a combination of some or all of them, wherein reference is made to the corresponding portions of the above description of FIG. 2.

Figure 4A:
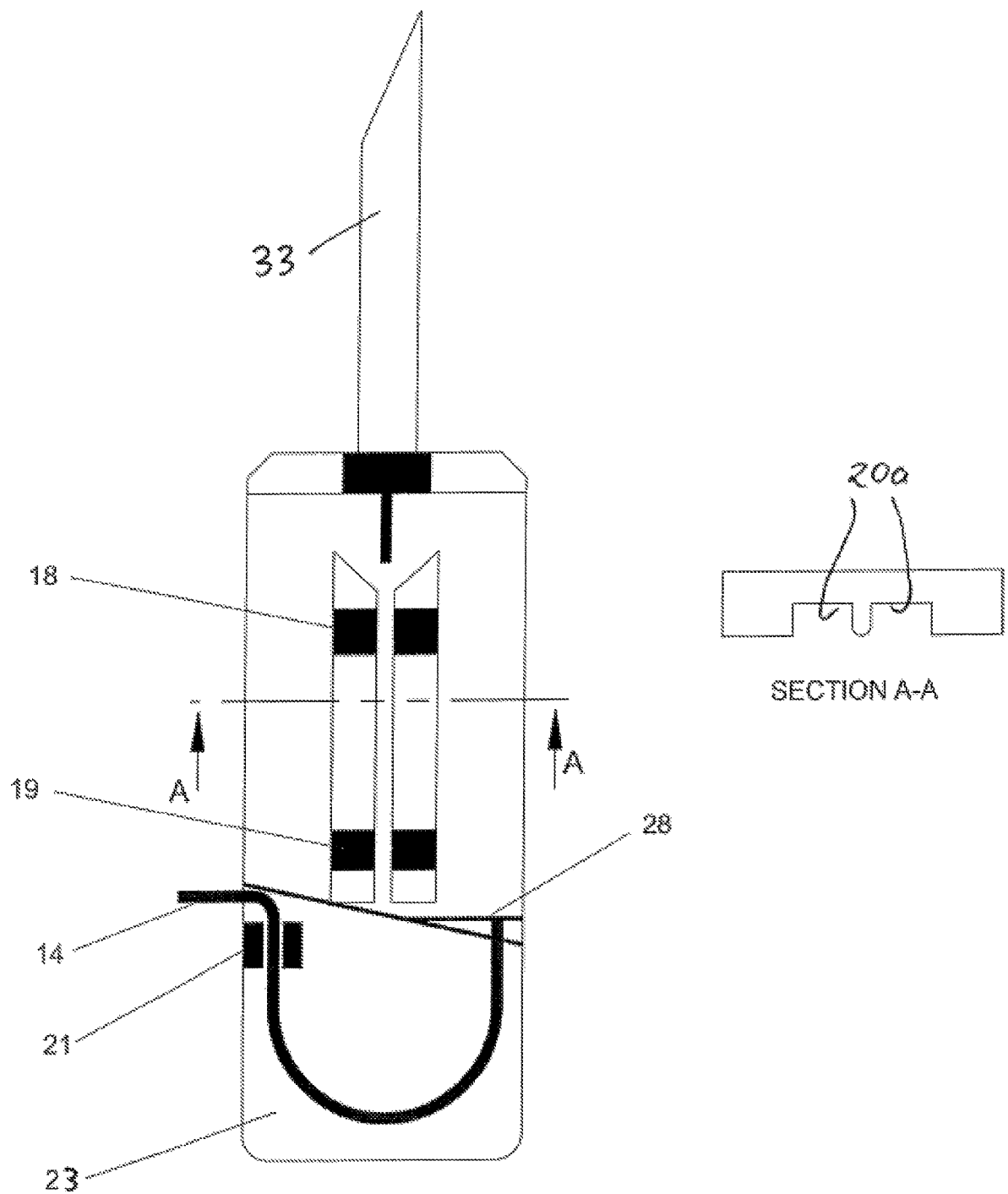
FIG. 4a schematically shows a drip-chamber-rotary-peristaltic-pump part with a spike provided as a consumable part according to a second preferred embodiment.

FIG. 4a shows a drip-chamber-rotary peristaltic-pump part as a cartridge being similar to that of FIG. 4 but having a spike 33 instead of a connector to be inserted into the reservoir (not shown in FIG. 4a) so that all the weight of this unit hangs down from the reservoir through the spike 33. Further shown is a section through the drip chamber 20 along a section line A-A in order to illustrate the above mentioned drip detector cavities 20a. As to all the other components shown in FIG. 4a, either only one of them or in a combination of some or all of them, reference is made to the corresponding portions of the above description of FIG. 4.

Figure 4B:
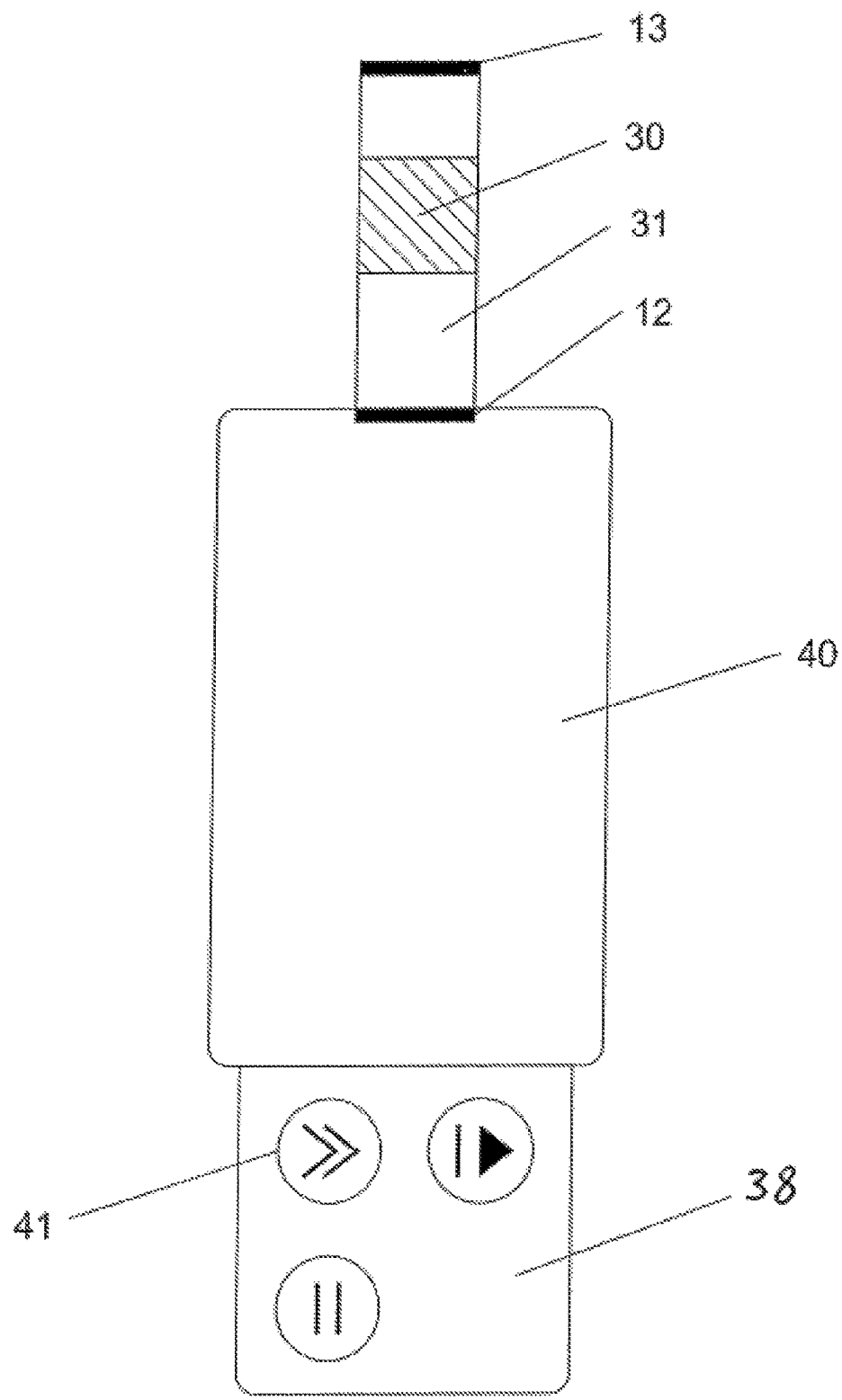
FIG. 4b schematically shows a front side of an infusion pump according to a preferred embodiment.

FIG. 4b shows a front side of an infusion pump 38 comprising an e-paper touch display 40 and a keyboard 41 for sensitive actions as well as on its top the camera 12 and the lever 31 with the inclined mirror 30 and the sensor 13 for low level drug detection. As to all the other components shown in FIG. 4b, reference is made to the corresponding portions of the above description of FIG. 4. Finally, all further components shown in FIGS. 2, 4 and 4a but not shown in FIG. 4b can also be provided in the assembly of FIG. 5, either only one of them or in a combination of some or all of them, wherein reference is made to the corresponding portions of the above description of FIGS. 2, 4 and 4a.

Figure 5:
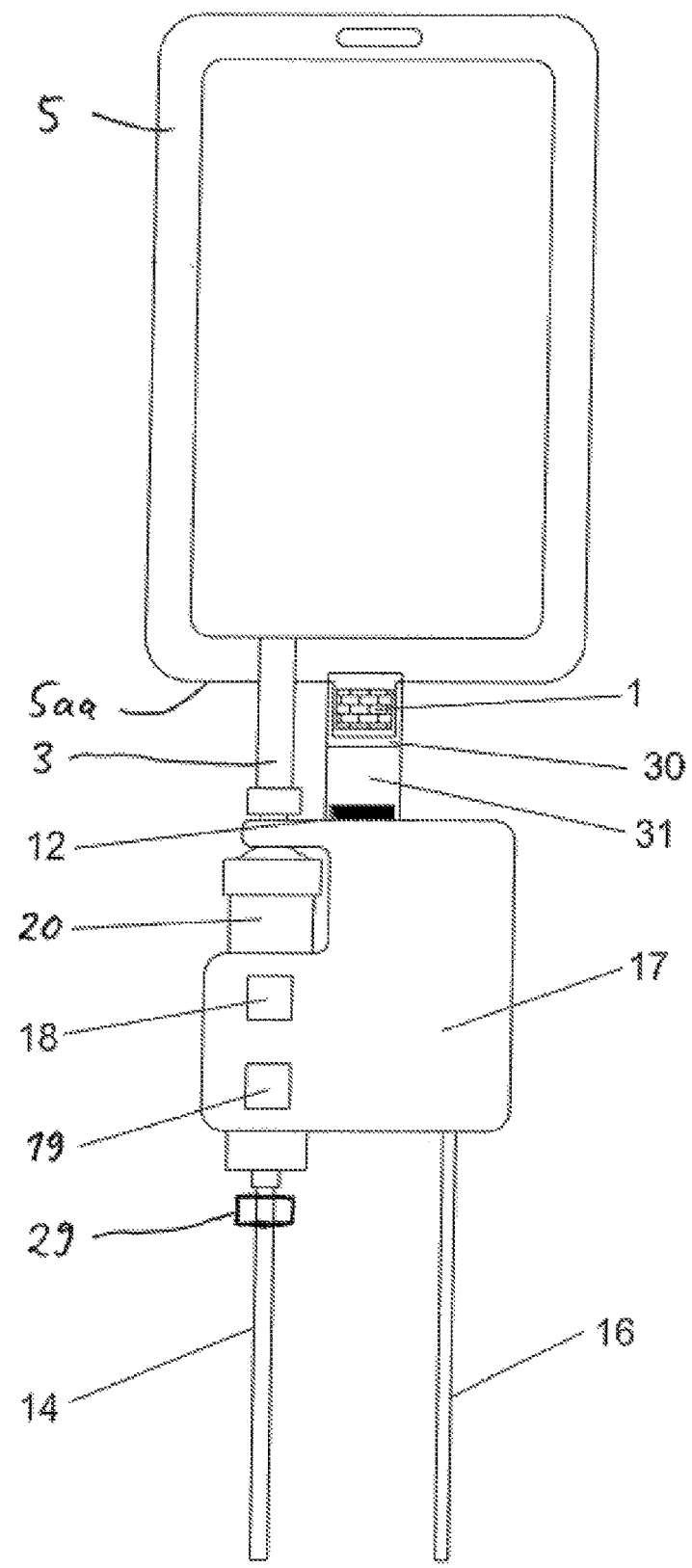
FIG. 5 schematically shows an infusion safety accessory kit according to a further preferred embodiment.

FIG. 5 shows an infusion safety accessory kit 17 for an infusion pump (not shown here) wherein the infusion safety accessory kit 17 is arranged at the drip chamber 20 which is coupled to the connector 3 of the reservoir 5. The infusion safety accessory kit 17 includes the drip sensor 18 for detecting drops and the low level in a drip chamber low level sensor 19, and is further provided with the camera 12 which is oriented so as to view upwards and the lever 31 having the inclined portion at which the mirror 30 for periscope action is provided for reading the barcode label 1 at a lower border of the reservoir 5. As to further details regarding in particular the reservoir 5 and its connector 3, the sensors 18 and 19 and the drip chamber 20 reference is also made to the corresponding portions of the above description of FIG. 2; and as to further details regarding in particular the barcode 1, the camera 12, the lever 30 and the mirror 31 reference is also made to the corresponding portions of the above description of FIG. 2a. Finally, all further components shown in FIGS. 2 and 3 but not shown in FIG. 5 can also be provided in the assembly of FIG. 5, either only one of them or in a combination of some or all of them, wherein reference is made to the corresponding portions of the above description of FIG. 2 and FIG. 3.

According to the present invention an intelligent medication-to-pump-connection accessory, as shown in FIGS. 3 and 5, is provided, while the description of the safety features herein also applies to a safe infusion pump/reservoir combination as shown in FIG. 2, comprising several sensors 13, 18, 19, 21 combined in a preferably serially communicating unit with the pump. The sensors can also communicate in parallel with more cables resulting in more weight and cable size. The communication and/or the power can also be provided wirelessly. The accessory kit 17 has a hole or a hook to be kept hanged from the hook of a pole 7 when not in use, so that the cable 16 does not need to be thick and curled as with a drip detector in conventional pumps. The batteries are wirelessly charged from remote through an antenna and high efficiency magnetic resonance or an electromagnetic means which are commercially available from Air Fuel Alliance companies; such batteries may power the device and the wireless charger, and an antenna emitter can be provided at the pump which is usually powered by stationary mains. The data can be wirelessly communicated through Bluetooth Low Energy or WiFi or other available technologies pairing the safety device with the pump. Data can also be transmitted through e.g. a high frequency over low frequency power so that resonance occurs at power transmission frequency, but lower power as needed for data can be transferred on a different frequency and filtered at the reception side, so that the system can be implemented on the transmission side and the battery charger on the reception side as a combined unit.

The accessory kit 17 can be connected to a serial port of the pump to be upgraded or to the same port used today for a drop sensor, provided the software upgrade in the pump analyses the data communicated.

The small and lightweight accessory kit 17 is preferably arranged at and around a conventional drip chamber 20 or a new type of drip chamber, as shown in FIG. 4a, and provided with a spike 33 and comprises a tag reader or camera 12 and one or more of the following parts (most of them can be used by a pump) for detecting possibility and time of a change of the reservoir 5 so as to force a tag reading and to avoid any mismatch of the drug with the infusion protocol:

A. A drip detector 18 preferably embodied as an optoelectronic detector for conventional drip chambers or as an ultrasound detector for a new type drip chamber shown in FIG. 4, and sensing each drop passing, so as to detect the flow for infusion. Alternatively, an active valve 29 (FIG. 3) at the bottom end of the drip chamber can stop the flow if activated. In case drops stop for some time, a reading of the reservoir tag is expressly done after a restart of the flow, for the possibility of a reservoir change, and if the medication is the same according to the prescription, in case the reservoir is detected to have been changed, the pump asks whether the last VTBI needs to be programmed automatically (by verification from a nurse) or changed to a new VTBI read from the tag if the reservoir 5, 6 is bigger or smaller. In case the pump starts infusion, but drops do not start at almost the same time, then the pump issues an alarm indicating a wrong reservoir connected to the pump.

B. A drip chamber low level detector 19, preferably embodied as an ultrasound detector, at the bottom of the drip chamber 20 to sense the presence or absence of the liquid so as to prevent air ingress into the infusion line, since in case of sensed air (i.e. in case of low volume) the pump generates an "empty reservoir" alarm after digital filtering of the signal in order to exclude false alarms, wherein, the pump forces a tag reading in case the reservoir is replaced after having been refilled.

C. A drug label or tag 1 facing the tag reader 12 which is preferably a miniature barcode reader comprising an RFID/NFC or a camera or a combination of both and is positioned in such a way that it can read anytime the drug label after fluid connection. This may be done by a periscope arrangement as shown in FIG. 2a from the pump wherein the camera 12 and the inclined mirror 30 are positioned on the top at label level, or a camera having a close-up lens mounted vertically to face a tag arranged at a wall surface of the reservoir 5 as shown in FIG. 4. The reader 12 reads the tag at setup, start of infusion and preferably also frequently or at larger time intervals during infusion, depending upon if the pump is supplied by mains or battery power. The reading is expressly done in case of a reservoir change sensed by motion sensors or by a drip detector 18 sensing a stop of dropping or by a reservoir level detector wherein the reservoir is then to be refilled, or by totally sensing no fluid in case of the absence of the reservoir, or by detecting a low level in the drip chamber 20 after having refilled the reservoir. The barcode reader camera 12 may also authenticate the patient and the therapist by a bar-code but also by a biometric photographic capture and an analysis done by a distant server.

D. A reservoir low level detector 13, 13a positioned at a specific place or position on the bottom of the reservoir 5, 6 to indicate a remaining low volume to be infused. The bottom of the reservoir may have a specific portion 5a, 5b with a restricted width B calculated from the total volume of the reservoir and with a height A and depth being equal and therefore standard for all reservoirs so as to define the desired volume below the level sensor 13 for alarming of the pump not only through a VTBI minus VI calculation as in the prior art but also from the reservoir volume itself, thus easing simple fluids infusion, normally given through gravity, by simply programming only the rate and not also the VTBI as in the prior art, except if the lower volume from the reservoir totality is needed. The tag 1 includes the information of how much is this special measuring volume that can be a few ml for low rate infusions up to 167 ml for a 1000 ml reservoir volume and abnormal infusion rate of 1000 ml/h. The width B is only changed for different reservoirs to define low level volume to be detected, whereas the sensing is done at the same distance or height A from the bottom of the reservoir at a reading point 2 (FIG. 1). The pump knowing the volume below low level alarm from the reading of the tag (or through drug library pointed by the No. read) and of the rate of infusion will alarm the near end of the remaining volume at an appropriate time, usually 10 min, to allow the nurse to replace the reservoir in time.

E. An electronic processing unit that gets power from a serial interface and combines the data from the aforementioned elements into a single communication serial line using protocols known in the art. The communication and the power can also be wireless by using a high efficiency power transmission (Air Fuel Alliance) and Bluetooth low energy or a similar technology for data transmission.

F. An LED indicator 10a that flashes e.g. blue or green at each drop sensed, and preferably combined with a small LCD display showing drops/minute and an "empty reservoir" flashing alarm or a "wrong connecting drug" flashing alarm to ease to nurse on finding which reservoir is to be replaced from a plurality of reservoirs hanged on same pole. So, in case of a drug related alarm the LED flashes e.g. in red color to indicate the nurse where the problem is among possibly many reservoirs hanging on a pole. Also the LCD display shows to which pump a reservoir is connected so as to ease handling.

G. A tilt and/or accelerometer sensor 8 showing that violent movements like unplugging a connector or a spike from a reservoir 5 or unplugging an accessory from a drip chamber 20 occur, to signal such events to the pump and to cause reading a tag. This sensor is not necessary if a low level reservoir detector 13 is provided which detects air when a reservoir is removed so as to signal the pump accordingly for causing it to read the tag when the reservoir is replaced and the detector 13 indicates the presence of liquid.

H. The drip chamber 15 provided with detectors showing an unplugged or plugged state of an accessory to a drip chamber so as to cause the reading of a tag as a plug-unplug-plug sequence indicates a possible reservoir replacement.

I. An active valve 29, as an alternative kit, closing the infusion line or tube 14 just after the drip chamber 20 (FIGS. 3 and 5) allows a drug infusion sequencing. Alternatively, to the active valve, a miniature infusion pump module (just what is needed to rotate the cassette mechanism) can be used as known in the art, and in such case the "pump" on the pole is replaced by a display-pump controller for multiple pump module-sensor kits.

The tag reader 12 has a cable 16 with enough length so that it can also scan a patient and a location label (Care Area) at an adjacent surface portion of the respective reservoir for "5R" (Right drug, Right patient, Right protocol, Right time to infuse, Right infusion site) checking at infusion setup. The barcode camera 12 may also capture biometric data, and an analysis done by a distant server or in the future locally as technology permits it. Care Area is correlated to correct the drug library used by the pump to assure protocol correctness.

The accessory kit 17 hangs down from the drip chamber 20 plugged with its spike 33 into the reservoir tubing, i.e. in the same way as drop counters do today, but having much higher functionality. For a multiple pump system or piggy-back infusions (one pump for two reservoirs), the cable 16 can be one cable from the pump going in line from one accessory kit to the next one in series at the lower reservoir level on each drip chamber 20, so as to have all data in a network arrangement and thus to reduce the number of cables mixing with infusion lines.

According to the present invention it is selectively added an active valve to the sensor kit in order to allow sequential infusions from a single pump. This is the case for a chemotherapy 8 drugs sequence that are infused by the same pump one after the other. So, in such case eight upstream infusion lines are joined to one infusion line upstream passing through one pump, and eight serial data lines are also connected to the same pump (preferably connected each one to the next one as described above) and to each sensor kit at each drip chamber. The pump knows which valve is associated to which reservoir and, hence, for which reservoir only this valve opens whereas all the other valves are closed and carries out an infusion at a prescribed rate for the programmed volume to be infused.

The active valve 29 (FIGS. 3 and 5) can comprise jaws which are closed by a micro gear motor and are clipped over the infusion tube 14 at the end of the drip chamber 20 so that energy is consumed only during the switching procedure, but not during operation, while other technologies common in irrigating systems can be used.

The valves can alternatively operate without the drip detectors as known in the art in cooperation with a drug tag reader, wherein an upstream occlusion indicates that the valves are closed, as described in prior art.

The accessory as described above provides a Medication Error Prevention and an Air in Line Avoidance covering all the following risk management cases:

1. The nurse places an infusion set to pump A and connects the spike of this set to reservoir I. Then, the accessory connected to pump A is taken away from a hook on top of a pole and placed to a reservoir II. The pump reads the tag of drug II and is programmed accordingly. Then nurse starts the pump to RUN but drops are already dripping or do not drip at all, wherein it is correct to just start from no dripping to dripping. So erroneous spiking is detected and a "wrong medication" alarm is output.
2. The nurse places an infusion set to pump A and connects the spike of this set to reservoir II. Then, the accessory connected to pump A is taken away from the hook on top of the pole and placed to a reservoir I. The pump reads the tag of drug I and is programmed accordingly. Then the nurse starts the pump to RUN but drops are already dripping (by means of another pump) or do not drip at all, wherein it is correct to just start from no dripping to dripping. So, erroneous spiking is detected and a "wrong medication" alarm is output.
3. The nurse removes the spike of the accessory as mounted from the reservoir containing the drug I while the pump A is running and infusing the drug II. The pump recognizes a discontinuation of the drops and possibly even drip chamber level detector transients. Also the tilt sensor shows violent acceleration and movements, so that in any of these cases the pump carries out an emergency reading of the drug tag and determines a different drug or the same drug (if the same drug but a new reservoir having replaced the old one). Then in case of a different drug it issues a "wrong medication" alarm. In case a reservoir low level detector is in place, a "low volume in reservoir" signal is issued, also drops stop, and the pump carries out an expressly tag reading when a low volume is restored.
4. The nurse removes the accessory and unplugs the spike and plugs it to a new reservoir and then places the accessory at the same drip chamber again. The grip detectors (and possibly all other detectors) indicate an unplug and re-plug state, so that the pump carries out a tag reading and issues a "wrong medication" alarm if the drug is different.
5. During such a handling as in the above cases, or in case the reservoir is nearly or completely emptied, air is entering and accumulated into the drip chamber. A first low volume in the reservoir detector signals a warning. Then signals may be generated due to a discontinued drip sequence so that the pump will alarm End of Volume. Then if the Drip Chamber Level Detector is signaling air, from one or the other or a combination of such states, the pump stops and gives an "excessive air in drip chamber" alarm for the nurse in order to replace reservoir and hence the drug, to press the semi-rigid drip chamber expelling air into the reservoir and to refill the reservoir with a new drug to the agreed level into drip chamber. Thus, air in the infusion line and a disconnection of the patient are avoided. A correct medication is checked at the start of the infusion (after a stop or a forced stop following alarm) in any case, and a medication error prevention is guaranteed.

For 5R determination the barcode reader 12 at the accessory kit 17 or the pump controller or the pump may determine the drug, but also an authentication for the patient and users reading barcodes by also capturing biometric data, sending them to a server and getting back ID data for 5R checking. The kit and the pump for this may have a biometric read button to instruct the camera to capture data at a correct position, while the barcode reading is automatic. In case the memory and the processing capabilities permit it, the biometric identification may be done locally, so that the button is not needed, as a human ID is also given automatically.

The present invention provides means to detect when a reservoir is changed and so to initiate the reading of the tag 1 in order to prevent continuation of a previous infusion with improper medication.

The flow sensor 18 may sense a reservoir change if the flow is stopped for some time before or due to a reservoir change. In such a case, a new reading of the tag is done when the drops restart or the pump restarts.

The present invention further provides means to prevent air entering into the infusion line, first by a low drip chamber level detector 19, and furthermore by detecting with the same sensor 19 when there is a turbulence in the drip chamber by having the option to stop the infusion temporarily until the turbulence is calmed. A list of drugs according to which this is not permitted assures life by sustaining short half-life drugs not to be interrupted. An infusion set type detector preferably for an infusion set connector or cartridge neglects any turbulence in case an air eliminating filter is in line. Said turbulence detection means may be one or combination of means for stopping the drops for a time window, tilt/acceleration sensors showing large movement, and the low drip chamber level detector before the digital filtering when detecting a momentary low volume level for more than one time in a time window. This is particularly helpful as nurses usually do not stop infusion when changing reservoirs and patients walking in a corridor may hit the reservoir resulting in turbulences in the drip chamber, so that portions of air pass into the line. Air is then detected by the Air In Line detector 21 downstream but this has to be avoided as it needs disconnection of the line from the patient with a high risk of contamination.

In case a pump hangs down from the reservoir without a drip chamber, a contact sensor for a reservoir tag plate or the reservoir tube connector or the reservoir itself can indicate the presence or absence of a reservoir and may then initiate a reading of the tag after restoring the presence of the reservoir. Alternatively, a low level sensor or a full volume sensor as described below can be used for reservoir presence detection.

The reservoir preferably comprises, besides the specifically positioned tag to be "anytime read", also a lower part with the restricted width B and the standard height A and depth wherein the volume within said lower part of the reservoir is close to the near end volume for issuing an alarm that the nurse has enough time to replace the reservoir with a new one. According to the present invention, there is a standard height A of sensor measurement for all sizes of reservoirs, determined by extending the pump or kit upwards to the sensor itself or by means of the length of an arm 31. The differing width of the lower portion 5a, 6a of the reservoir 5, 6 provides small volumes for small reservoirs or big volumes for big reservoirs that usually run at higher infusion rates. The sensor 13 reading the level of the liquid at a specific constant reading point is combined with the camera 12 or the periscope mirror 30 for reading the barcode label 1 at the same height or lower. The width B is such that the needed height A for the volume to be sensed is enough in order to avoid false alarms. The pump can calculate the time to alarm "Near End of Infusion" (NEOI) from the sensed volume and the infusion rate so that the remaining infusion time is according to standards. In its simplest form the low volume compartment 5a, 6a can be a U shaped volume (A to B) as in all reservoirs today for collecting fluid at the connector 3, where the U lower sealing slope is varying for each nominal volume so that the volume at the constant reading point 2 is the one close to the "Near End of Infusion" alarm. For even more safety against false alarms, the gate on top of the lower volume may not be completely open but restricted to a path that even allows the flow by gravity easily, but filters sudden big volume transfers in case the reservoir is transported and balancing. Even better, the lower portion 5a, 6a of the reservoir 5, 6 defining the low volume compartment as described may have the vertical bond strips 25 on its walls (FIG. 1) as an array of vertical tubes open at their bottom for a communication with the fluid from below and on top for an escape of trapped air to the main portion 5b of the reservoir 5 and for filtering liquid movement from one side to the other. These parallel tubes filter even better the fluid level reading mechanically before its digital filtering. The entering gate (not shown) may have a V shape above it towards the main portion of the reservoir in order to collect the last fluid above by gravity drain, and the shape after the entrance may also have a reverse V shape or a portion that is narrow at the sensor reading point so that the liquid level lowers due to the infusion faster than in the lower larger part, and hence level perturbations will cause less erroneous readings. The sensor kit comprises an ultrasound fluid level detector 13, 13a at both sides or a capacitive fluid level detector 13 (US2005/0172712A1) at the front side directed upstairs where the respective part of the reservoir is arranged inside or touches it with some small pressure (FIG. 2b), and hence the top of the U with the two facing ultrasound detectors (receiver-transmitter) is positioned at the level of the near end of volume of reservoir or a vertical capacitive sensor (not shown) gives a volume information as it decreases. So after spiking the reservoir 5 with a spike 33 integrated with a drip chamber 20 (FIG. 4a), the kit is positioned by first placing the U sensor part 13, 13a (FIG. 2 and FIG. 3) over the lower portion 5a of the reservoir 5 with the restricted width and then gripping over the drip chamber 20 by means of spring retainers passing over 180 deg. of its diameter for a few degrees more at one or two points. This way, all sensors are in a correct position for drip and level and tag reading.

In another preferred embodiment, a long capacitive fluid level detector 15b (FIG. 2a) extending from the top to the bottom of the reservoir is provided with a plurality of capacitive conductive pattern pairwise elements (US2005/0172712A1) connected in parallel so as to enhance their capacitance and separated from each other in height in an equidistant arrangement. The separation may be of several ways, wherein the detector is preferably easily bendable so to follow a curvature of the reservoir and maintain contact with its surface all time. An elastic belt may be provided wherein the conductive patterns and connecting conductors (tinsel wire for bending without breaking) are embedded in the woven material of said belt so that when elongating the belt the distance between the capacitive pairwise elements increases. Further, two rulers may be provided for sliding out for expansion and coming close for retraction. In another preferred embodiment a conductive rubber strip with two conductive rubber layers and one insulator therein between in S form wherein the conductors are alternatingly arranged in a vertical orientation and a horizontal orientation and cuts are alternatingly arranged from left to right so that said strip may extend for larger reservoirs 5 and restrict for smaller ones 6 (FIG. 1), and while being elastic envelops the curvature of the reservoir in contact with its surface using two points at its extremities that are forced against the reservoir on its top adjacent to the hook and at its bottom with the tag. The capacitive conductor pairwise elements can predict for both small and big reservoirs the percentage of the fluid in them (equivalent to how many patterns are in contact with the fluid or drug and how many are not). When decreasing the capacitance, as fluid is infused, the pump takes decisions accordingly. The percentage of length may be converted to percentage in volume by a calculated or experimental table or to curve volume/% for several basic reservoir packages wherein this curve gives more volume per some percentage in the center than in the extremities due to the curvature of the reservoir. The pump then knowing the size of the reservoir from the tag reading and the percentage of filling can calculate the volume in the reservoir. So, in case of a sudden capacitance change, a tag reading is done and hence the medication is detected. If the capacitance is as before, the infusion can continue. In case the capacitance is high as with a full reservoir, the VTBI is proposed by the pump as the volume given in the tag, with the result of easing the programming. In case the capacitance is low, the pump gives an alarm indicating a near end of the infusion or an end of the infusion depending upon reading the tag, so that in case of a different medication a medication error is prevented and the pump stops the infusion and proposes attributes read from the tag for programming with comparing them from prescriptions pending for the same patient. This level sensor may replace tilt/accelerometer and drip chamber contact sensors so as to sense when a reservoir is replaced. The sensor can be normally hanged all the time down from a hook of a pole, and on top of it the nurse hangs the reservoir (so that the top of the capacitive sensor is placed), then plugs a spike or connects a connector of the infusion set and changes the form of the belt, in particular elongates it to attach the sensor kit at its end over the drip chamber, by also facing the reader to the reservoir tag so that the bottom of the capacitive sensor is also placed correctly and the belt is bent around the curved surface of the reservoir assuring a good contact and a good capacitance effect from the fluid within the reservoir. Because of the elongated form of the sensor hanging down from the pole hook, the tag sensor can also be arranged at the top of the reservoir on its border or its surface, and the tag reader can be arranged on the hook part and wired with the drip chamber sensor part and then the pump. This is advantageous due to a reduction of the hanging weight and due to the fact that any complication of communication cables does not increase if the cables are following the capacitive pattern integrated in its structure.

Alternatively, a load cell 15a (FIG. 2) measuring weight electrically/electronically connected with the whole assembly can be hanged down from the pole 7 and the reservoir 5 from said load cell 15a, so that it can monitor any weight changes of the hanged reservoir 5 pretty much in the same manner as the capacitive sensor but with a direct reading of the volume. Sudden changes in weight induce a reading of the tag to detect a possible reservoir change.

The pump programming may be simplified by the present invention. In prior art, the Volume to Be Infused (VTBI) is first programmed in association with the Infusion Rate or Infusion Time. Then the pump calculates the Near End of Infusion and the End of Infusion warning and alarm points as well as, if needed, the following Keep Vein Open (KVO) infusion using the lowest possible infusion rate and the associated volume. According to the present invention, thanks to the sensing of the initial volume, the near end of the infusion and the end of the infusion, the nurse (if there is no prescription available) can just program the time of infusion, and the pump can operate safely until the end of the available volume since the pump has means to detect the infusion progress to even check that the liquid consumption is in line with the programmed one and hence to double check upstream occlusion sensors and an infusion "lid open" sensor or a defect or damage of the infusion pumping segment or pumping mechanism that all may affect infusion accuracy. This is checked by drops/minute and also a reduction of the volume in time, and the near end of the infusion and the end of the infusion are detected by level sensors wherein the dripping is stopped after a level alarm as described herein.

The level sensors 13, 19 cause a sequence of alarms as the volume is decreasing. First, after digital filtering of its readings (to avoid false alarms from a balancing reservoir) the Near End of Volume sensor 13 gives an alarm for the pump to set a warning with an orange light flashing on the kit for the nurse to replace the reservoir after calculation of the remaining time until the end of volume in it calculated from the volume which is detected by the level sensor and known from the reading of the tag and the rate of infusion. Second, after this first warning a repeated (also digitally filtered) "drip absence" signal indicates that the reservoir 5 is depleted, and the pump should give an "end of volume" alarm but may continue infusing (policy for alarms may decide on this) until the low level of the volume given by the drip chamber alarm, when the pump stops so as to prevent air coming into the line and continues alarming.

According to the present invention, it is presented at least three ways to detect reservoir change: (1.) by means of a tilt and/or accelerometer sensor 8 combined with a drip chamber contact sensor 9 (FIG. 2) to sense the unplugging or plugging of a spike or connector, (2.) by means of a low volume portion or chamber 5a, 6a (A to B) below the reservoir 5, 6 and a level sensor 13 at a specific height A wherein the width B increases the sensed low volume (for higher infusion rates) at the same sensing height, and (3.) by means of a belt type capacitive sensor that can sense a percentage of volume in the reservoir and the absence of the drug or liquid when the reservoir is changed, while any of these three solutions can be combined or separately used. The third solution is also suitable for thin wall bottles and for reservoirs that cannot be sensed with the sensor being disabled.

Alternatively, the sensor kit comprises a jaws joint at below, the reservoir border has holes to orient the clipping of the jaws at the correct level and position, the top of the drip chamber has not a spike but a pin to enter and is fluidly connected with a swabable connector extending down from the bottom of the reservoir, the tag 1 of the reservoir 5 is arranged on a tongue 4 hanging down from the border 5aa of the bottom of the reservoir 5, and the tag reader 12 on the sensor kit comprises a square pyramid thin wall black optical guide, on top of which is located the camera reading barcodes, while an antenna reading RFID tags is located on the periphery of the base of the pyramid just over a further antenna of the RFID tag.

The tag 1 can also be a memory chip of standard or organic electronics that can be placed on or adjacent to the fluid connector 3 and powered and read serially by contacts on the fluid connector from the pump side anytime so that any disconnection and connection is immediately sensed. Organic electronics today already have advanced and have become suitable to form a commercially available memory so that it can be printed on a label at the connector position of the connector. The power to read is much lower than with a barcode or RFID, and powering it even without reading can be a measure to sense if a disconnection or connection happens. A special connector according to the therapy/delivery route can be used as a further safety means, as its infusion set type is recognized by the pump. The pump side connector has two or three golden pins and the connector at the reservoir side has two or three contact plates that come in contact when a fluidic connection happens. This preferred embodiment does not use tilt or accelerometer sensors for sensing a reservoir change but can use these sensors for stopping the infusion temporarily in case a transport balancing happens to avoid air to pass into the line accidentally as during this the drip chamber may not have a stable fluid level.

In order to connect this new reservoir and sensor kit assembly, the nurse places the drip chamber 20 at or in a cavity of the kit 17, then places the pins into the holes of the border of the reservoir to locate correctly the kit, and closes the jaws securing preferably with a secondary action of the lever. By doing this, a number of things happens simultaneously: The fluid connection between the swabable connector 3 of the reservoir 5 and the drip chamber pin is established with no leakage, the tag is enclosed by the optical and electromagnetic faces of the square pyramid from one side and a back plate from the opposite side so as to be completely secured, the sensor 13 for detecting the near end level of the volume, and the drip sensor 18 and the drip chamber sensor 19 all are placed in a correct reading position. The pyramid completely encloses the label or tag which can be read correctly from a distant reading point of view with the LED illuminating without being noticed from the outside, so as not to disturb the patient. Said square pyramid may be also bent by 90 deg. having a mirror at the bending point oriented with a 45 deg. angle so to work as a periscope wherein the camera 12 is directed upwards so as to read a vertically oriented label or tag 1 on the reservoir 5, thus reducing size of the kit. Alternatively, a camera 12 with a special wide angle lens and a short distance reading capability directly facing the barcode tag 1 can be used.

The reservoir 5, 6 according to the present invention is made for pharmaceutical prefilled fluids and drugs, for pre-filled saline or dextrose intended to be mixed with drugs at the pharmacy/compounding premises, and for empty reservoirs that will be completely filled at the pharmacy/compounding premises.

The label 1 for compounding may be printed by a normal printer for generating a barcode or an RFID printer for generating an RFID. A printed self-adhesive label comprises two sections, a larger printed area with a wording of contents and a classic barcode from the pharma industry to be placed on the surface of the reservoir and a smaller printed area at the corner of the printed label is preferably provided as a QR (square barcode) to be placed on the lower border at a specific place or on the surface inside the lower low level volume portion 5a, 6a A-B of the reservoir 5, 6 as shown in FIG. 1, a common place for all reservoirs used, so to be read by a safety device, a pump or an accessory kit 17. Holes in the border and the label itself help bonding the adhesive label in a correct position by coinciding both the label and reservoir holes so to be read correctly by the tag reader of the sensor kit. According to the present invention, for safety the drug labeling and tag reader 12 are used in cooperation in a drug device combination, so that the relative positions of the tag reader of an infusion management device and the tag 1 at the reservoir or bottle are the same by facing each other for any reservoir size so that reading is possible any time during infusion. So, any options described herein like the arrangement of the tag on the border 5aa or the surface of the reservoir 5 or on the connecting tube or at the hanging point, if selected, require that the associated infusion safety management device (pump or flow sensor or active valve) has the reader 12 located at a constant position for reading the tag 1 for any reservoir size.

Alternatively, the present invention can be used with less safety but better than conventional pumps, by scanning the conventional tag by hand by said infusion safety management device and then immediately plugging it on the reservoir, so that safety is somehow achieved by positioning the infusion management device in vicinity of the reservoir.

In another preferred embodiment, the pump comprises all sensors described above so that it can draw fluid from a reservoir 5 close to it, wherein the bottom of the reservoir 5 is arranged in reading distance of all sensors for low level fluid in the reservoir 5, drip chamber drip and low level fluid and the tag reader 12, wherein the top hook can be adjustable in height as many solutions exist for this doing.

According to a further another more advanced embodiment, the medication reservoir is arranged just above the pump module of an LVP, and the drip chamber is enclosed by the same secure door that also fluidly connects a swabable connector of the reservoir to the connector on top of the drip chamber. One single movement of a lever for closing the secure door results in positioning the infusion segment of the tube against followers for infusion, pressure sensors upstream and downstream, an Air In Line detector relative to their readers as usual but also the sensors for drops and drip chamber level, the tag relative to its reader and the drug low level detector into its correct position on a lower reservoir, and fluidly connecting the top of the drip chamber with the fluid connector at the lower reservoir.

The drip chamber 20 is arranged in the pumping compartment 10 that has an opening just in front of the drip chamber 20 so that air can be compressed and expelled back to the reservoir 5, wherein this drip chamber portion is to be opened by the same door as the pumping segment. The reservoir change is sensed in this case not by accelerometers but by the low level volume in reservoir sensor which in case of a change indicates a low level of the volume of fluid in the reservoir so as to force the reading of the tag after a restore of the volume, i.e. renewal of the reservoir.

The connection to the reservoir tube is preferably done not by a spike but by a luer or another snap fit or press fit means, and the reservoir does not hang but is arranged preferably in a wire frame and on a U shaped level detector 13, 13a, wherein the wire frame can accommodate bottles and bags with a wider central portion.

So, there is a wire frame holder above each pump. Since the lower dimensions of the reservoir can be standardized for any reservoir size, all sensors and fluid connections are always in place. The tag 1 may be aside and close to the reservoir low level indication line. So, the lower reservoir part 5a of the reservoir 5 for low level indication sits within said U sensor 13, 13a, and the tag 1 on the border sits in a fence just opposite to its reader in form of a periscope. The pump may comprise one display and many pumping modules one after the other, doors and sensors within and on top of them each with a wire frame for their reservoir which is directly connected to the connector or spike of the drip chamber. The reservoirs cannot face as the display does in front but at an angle between facing and vertical orientation relative to the display so that large reservoirs can be accommodated in a short multi-pump length.

In a further preferred embodiment of the present invention a drug/device combination comprises a medication reservoir with:

First, an optional lower part 5a, 6a at reduced width for calculating a "Near End Of Infusion" (NEOI) alarm generated by the pump without the need to input the reservoir volume, thus easing programming, wherein the width (and therefore the volume) depends upon the usual infusion rate of the medication or drug and the size of the reservoir 5, 6.

Second, an open window at the level of the volume of fluid for the Near End Of Infusion (NEOI) normally at the full reservoir extended width line or the upper limit of said lower part 5a, 6a of reduced width, where reservoir walls engender and seal a soft tubing of a few mm up and down, allowing flow through it and sealing around it so that two holes appear one at each side of the tube, for Ultrasound reader plates to measure fluid level, wherein the distance from said window to the infusion connector 3 (or spike receptacle) at the end of the lower connecting tube of the reservoir is always the same at all reservoirs produced according to present invention irrespective of their size.

Optionally the window and the lower NEOI volume can be replaced by a simple tube of the same size as that inside the said window, which tube has the length (window to connector) defined above and terminated preferably at the connector. The size of the tube is large, preferably having a diameter of about 4 to 6 mm diameter. Further the tube is preferably somehow hydrophilic, so that it works as a drip chamber, allowing incoming air accidentally coming from above, when the reservoir is balancing, to escape back to the reservoir so that a continuous liquid flow into the pump infusion set is maintained.

Third, a barcode label printed or placed near to or on the lower border 5*aa* of the reservoir 5, readable from a hanging pump or upgrade kit through direct view wherein the camera 12 faces the reservoir border or through a periscope wherein the camera 12 views upwards to an inclined mirror 30. Alternatively, the placement of the barcode 1 on the reservoir 5 can be near to the top hanging hole position where the accessory kit 17 (FIGS. 3 and 5) or pump controller 11 (FIG. 2) is hanging, when there is no infusion, from the hook of the pole 7, and this same hanging system also comprises the tag reading camera 12 and means to face directly or indirectly (periscope) the label 1 at its position automatically when the reservoir 5 is hanging, as both the kit 17 and the reservoir 5 have the same hanging position hook and therefore the same relative position reference, connecting for data and power with lower flow regulation or detection and other safety means as described herein.

The infusion pump is placed proximal to the reservoir, preferably hangs down from it and comprises a connector or optionally a spike to connect its infusion set (that preferably is a mechanism cassette) with said end reservoir connector, from which according to one aspect of the present invention the low weight pump is hanging, whereas according to the other aspect of the present invention the pump supports the reservoir in an upward or inclined orientation, wherein such pump comprises:

First, an ultrasound level detector 13, 13*a* that is placed at the specific distance from the connector 3 upwards, so as to enter said window open in the reservoir 5 to enclose the tube at the middle of the window or said optional tube in case of the absence of the window and a lower volume. It detects the level of the fluid/drug and gives the NEOI alarm in a first case after a calculation from the actual infusion rate and the lower available NEOI volume alarm, and in a second case with the absence of the window and the lower volume immediately so as to prevent air to enter the infusion set and to avoid complications for priming the air. In the second case, the tube can be pressed by hand in order to refill the tube with a medication or drug in case of a false alarm and available medication in the reservoir, much the same procedure as usually done to refill drip chambers. In any case, according to the present invention, air is stopped before the connection point between the reservoir and the pump set. The level detector grips over the tube at a second point to hold the pump or the upgrade kit 17 in the same manner as with the barcode reader 12 since the reservoir 5 does not allow it to fall back so as to ensure the reading distance of the barcode 1 during the infusion.

The barcode label 1 indicates the pump controller 11 which type of reservoir is used, therefore which NEOI volume exists (lower volume), or that it is zero (tube only), additionally to all other attributes known in the art like name, volume, concentration, expiry date etc.

Second, a barcode reader camera 12 with a close up lens is placed at a specific point on the pump facing the barcode label 1 which point is determined by the distances from the connector 3 and the level detector 13. The camera 12 optionally can be arranged in a lower position at the pump wherein the inclined mirror of a periscope allows reading the label at 90 deg.

Third, a particles filter at the connector of the infusion cassette and a clear window on the back of the cassette to show the rotation of the mechanism according to the programmed infusion rate so as to fully comply with the functionality of a drip chamber in every of three aspects as it is preferred by the clinicians, i.e. the flow speed indication, the air prevention to pass into the line and the filtering of glass debris possible in the reservoir.

An upgrade kit 17 (FIG. 3) can be used with the same reservoir setup, that has a level detector 13 at the same distance from the connector 3 and a barcode reader 12 at the same triangle arrangement defined by the barcode, the level detector 13 and the connector 3 for the pump, but additionally has a flow detector usually in form of a drip chamber 20 connected to the reservoir connector 3, or an active valve 29 below the connector. The upgrade kit can be used with a conventional pump or for a piggyback infusion to ensure safety according to the present invention.

The present invention furthermore provides high accuracy and linearity infusion sets to be used with conventional pumps without any modification in case of drugs that need more accuracy and have a short half-life in the body.

So, it is provided new infusion sets to be fitted into existing pumps with accuracy as high as 2% and linearity as good as a syringe pump. For doing, so the pumping segment is made by silicone injection molding which by itself gives high accuracy and repeatability, but also has a larger diameter in a portion of it just starting at the moment of a well-known pulse, when in a rotary peristaltic pump mechanism the last roller disengages from the tube, so that its diameter goes back to normal when said roller is fully disengaged. The standard volume per revolution of the replacement tube is exactly the same as the replaced tube so that the pump can be used for both infusion sets with the same calculations.

The tag preferably for pharmaceutically pre-filled drugs but also for compounded ones can be placed at the reading distance from the reader of the accessory, directly face to face or through reflectors. So, a barcode label can be put in a vertical orientation to the reservoir border or the connecting tube showing towards the extremity of the tube so that the reader is arranged at the top of the accessory or the infusion pump so as to face upwards, or the label is arranged at the border or parallel to the border of the reservoir or on an extension hanging down from the border of the reservoir wherein the reader is securing a reading distance and is facing towards it, and is therefore arranged at the back of the accessory or pump. In case a reflector is used, the reader and the label or tag can face in different angles like 90 deg. and at 45 deg. with the reflector. So, even a classic label on a bag can be read by means of an extension reflector on the top of the accessory with a periscope like arrangement.

The invention claimed is:

1. An infusion safety device comprising:
    a tag reader adapted to read a medication tag provided at an infusion medication reservoir, in particular during the whole infusion;
    a processing unit connected with said tag reader and provided to be connected with an infusion pump in which an infusion protocol is stored and is adapted to recognize a change of the medication reservoir, to read the infusion protocol from the infusion pump, to cause said tag reader to carry out a reading operation in case it recognizes a change of the medication reservoir and to give an alarm in case there is no match between the medication read by said tag reader and the medication required by the infusion protocol; and a detector unit which is adapted to detect a change of the medication reservoir.

2. The device according to claim 1, wherein for the recognition of a change of the medication reservoir the processing unit is adapted to cause the tag reader to periodically carry out a reading operation and to recognize on the basis of the output from said tag reader whether or not a change of the medication reservoir has occurred.

3. The device according to claim 1, wherein said detector unit comprises an accelerometer and/or a tilt detector and/or a contact sensor adapted to detect a contact with an infusion system and/or with a reservoir tubing connector and/or a reservoir low level sensor adapted to detect a predetermined low level in the medication reservoir and/or a flow sensor adapted to detect a flow out of the medication reservoir and/or a drip chamber low level sensor adapted to detect a predetermined low level in a drip chamber.

4. The device according to claim 1, wherein said detector unit comprises a reservoir total volume sensor adapted to detect the total volume of the medication in the medication reservoir.

5. The device according to claim 4, wherein said reservoir total volume sensor is a capacitive sensor which is flexible and is hence adapted to come in contact with and follow a surface of the medication reservoir.

6. The device according to claim 4, wherein said reservoir total volume sensor comprises a load cell from which the medication reservoir is to be hanged down.

7. The device according to claim 1, wherein the device is provided to be attached to a drip chamber which is directly connected to an infusion medication reservoir arranged above the drip chamber and to be fastened to a pole in a higher position and is further connected to an infusion pump arranged below the drip chamber and to be fastened to the pole in a lower position.

8. The device according to claim 1, wherein a detecting unit which is adapted to detect and output read medication data and/or drops and drops per minute and/or an acceptable low liquid volume in a drip chamber and/or acceleration or tilt and/or attachment or detachment of the device to or from the drip chamber and/or a low level of medication in a medication reservoir.

9. The device according to claim 8, wherein an illuminating indicator is adapted to flash light in a first color for each drop detected in the during infusion and in a second color in an alarm state, wherein the first color is different from the second color.

10. The device according to claim 1, wherein a controller is adapted to cause the tag reader to carry out a reading operation and to determine the reading frequency both depending on if the power is supplied by the mains or by a battery.

11. The device according to claim 1, wherein said tag reader comprises an optical unit which is adapted to read the medication tag provided as a barcode on the surface of the infusion medication reservoir, and wherein an adjustment equipment is further provided which is adapted to adjust at least a part of said optical unit so as to enable it to read the barcode.

12. The device according to claim 11, wherein said optical unit comprises a camera which is adapted to directly face the barcode, and said adjustment equipment is adapted to adjust the viewing angle and/or the position, in particular the height, of said camera relative to the barcode.

13. The device according to claim 1, further comprising a tube which is adapted to connect the infusion medication reservoir with the infusion pump, a flow sensor detecting a flow out of said medication reservoir, and an active valve adapted to open or close said tube, wherein the tag reader is associated with said infusion pump and/or said flow sensor and/or said active valve.

14. An infusion safety device comprising a medication tag reader having an optical unit which is adapted to read a tag provided as a barcode on the surface of an infusion medication reservoir, wherein said optical unit comprises at least one mirror and a camera pointing to said mirror, and an adjustment equipment is further provided which is adapted to adjust the viewing angle and/or the position, in particular the height, of said mirror relative to the barcode so as to enable it to read the barcode.

15. The device according to claim 14, wherein said optical unit comprises a periscope including said mirror, wherein said adjustment equipment is adapted to adjust the viewing angle and/or the position, in particular the height, of said periscope relative to the barcode.

16. The device according to claim 15, wherein said mirror is removably provided.

17. The device according to claim 14, wherein said adjustment equipment comprises a holder supporting at least a part of said optical unit.

18. The device according to claim 17, wherein said holder comprises a lever having a free end which supports at least a part of said optical unit.

19. The device according to claim 18, wherein a camera is supported by said lever.

20. The device according to claim 18, wherein said lever is adjustable in its length or height and/or in its inclination and/or in its rotational position.

21. The device according to claim 14, wherein said periscope is removably provided.

22. The device according to claim 14, wherein said optical unit is adapted to be arranged at least partly below the infusion medication reservoir.

23. The device according to claim 14, which is adapted to be positioned close to the barcode so as to read it anytime at a start of the infusion or during an infusion.

24. An infusion safety device comprising:
a medication reservoir which includes a main volume portion and
a lower volume portion in fluid communication with said main volume portion and is arranged below said main volume portion when the medical reservoir is in its operational position,
wherein said lower volume portion has a width depending upon the total volume of the medical reservoir so that it is larger with a bigger total volume and smaller with a smaller total volume,
wherein said lower volume portion has a predetermined height which is the same with all medication reservoirs irrespective of their total volume, and
wherein said lower volume portion is provided as a low level volume compartment defining a predetermined low volume level for indication of a near end of an infusion as an alarm criterion.

25. The device according to claim 24, wherein the width of said lower volume portion is smaller than that of said main volume portion.

26. The device according to claim 24, wherein a low level sensor is adapted to determine the predetermined low volume level in the lower volume portion.

27. The device according to claim 26, wherein said low level sensor is provided at the outer side of said lower volume portion and further a processing unit is provided which is connected with said low level sensor and is adapted to recognize a change of the medication reservoir and to cause a tag reader to carry out a reading operation in case said processing unit recognizes a change of the medication reservoir so as to verify the content and level of the medication.

28. The device according to claim 26, wherein said low level sensor extends essentially along the full height of said lower volume portion, preferably at one side, and is adapted to indicate if there is the same medication reservoir or a new one and its remaining volume.

29. The device according to claim 24, wherein a fluid connector comprises at least one of a snap-fit connector, press-fit connector, Luer connector, and swabable connector, the connector further comprises a tube adapted to accommodate a spike which is provided at a drip chamber and further comprises a stop, preferably an end plate, for limiting the insertion depth of the spike into the tube to a predetermined distance.

30. The device according to claim 24, wherein the main volume portion comprises a filtering arrangement.

31. The device according to claim 30, wherein said filtering arrangement comprises sealing lines spaced apart from each other which extend in an essentially vertical orientation with the medication reservoir being in its operational position and define, preferably cylindrical, compartments being open on their top and at their bottom.

32. The device according to claim 24, wherein a tag is placed on a border of the lower volume portion.

33. The device according to claim 32, wherein said tag is placed just aside said predetermined low volume level.

34. The device according to claim 32, wherein said tag comprises a barcode and/or an RFID.

35. The device according to claim 24, wherein a tag is arranged below a border of the lower volume portion.

36. The device according to claim 35, wherein said tag is placed on a, preferably flat, supporting element, in particular a tongue, extending down from the border of the lower volume portion.

37. An infusion system comprising:
an infusion safety device comprising:
a tag reader adapted to read a medication tag provided at an infusion medication reservoir, in particular during the whole infusion; and
a processing unit connected with said tag reader and provided to be connected with an infusion pump in which an infusion protocol is stored and is adapted to recognize a change of the medication reservoir, to read out the infusion protocol from the infusion pump, to cause said tag reader to carry out a reading operation at the latest in case it recognizes a change of the medication reservoir and to give an alarm in case there is no match between the medication read by said tag reader and the medication required by the infusion protocol; and
a medication reservoir provided with a medication tag and which includes a main volume portion, wherein a lower volume portion fluidly communicates with said main volume portion and is arranged below said main volume portion with the medical reservoir being in its operational position,
wherein said lower volume portion has a width depending upon the total volume of the medical reservoir so that it is larger with a bigger total volume and smaller with a smaller total volume,
wherein said lower volume portion has a predetermined height which is the same with all medication reservoirs irrespective of their total volume, and
wherein said lower volume portion is provided as a low level volume compartment defining a predetermined low volume level for indication of a near end of an infusion as an alarm criterion.

38. The system according to claim 37, further comprising:
an infusion pump;
a drip chamber which is connected upstream to the medication reservoir and downstream to the infusion pump; and
a detecting unit adapted to detect and output at least one of read medication data, drops and drops per minute, an acceptable low liquid volume in the drip chamber, acceleration or tilt, attachment or detachment of the infusion safety device to or from the drip chamber, and a low level of medication in a medication reservoir.

39. The system according to claim 37, further comprising:
an infusion pump;
a tube connecting the medication reservoir with the infusion pump;
a flow sensor detecting a flow out of said medication reservoir; and an active valve adapted to open or close said tube, wherein the medication tag reader is associated with said infusion pump and/or said flow sensor and/or said active valve.

* * * * *

UNITED STATES PATENT AND TRADEMARK OFFICE
CERTIFICATE OF CORRECTION

PATENT NO. : 10,874,795 B2
APPLICATION NO. : 16/023860
DATED : December 29, 2020
INVENTOR(S) : Achilleas Tsoukalis Page 1 of 1

It is certified that error appears in the above-identified patent and that said Letters Patent is hereby corrected as shown below:

In the Claims

Column 23, Line 45, Claim 9, delete "in the.".
Column 24, Line 19, Claim 16, delete "mirror" and insert --periscope--.
Column 24, Line 33, Claim 21, delete "periscope" and insert --mirror--.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*